(12) United States Patent
Takato

(10) Patent No.: US 12,004,715 B2
(45) Date of Patent: Jun. 11, 2024

(54) OBJECTIVE OPTICAL SYSTEM AND ENDOSCOPE USING THE SAME

(71) Applicant: OLYMPUS CORPORATION, Hachioji (JP)

(72) Inventor: Hideyasu Takato, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 631 days.

(21) Appl. No.: 17/146,533

(22) Filed: Jan. 12, 2021

(65) Prior Publication Data

US 2021/0127956 A1 May 6, 2021

Related U.S. Application Data

(63) Continuation of application No. PCT/JP2018/033232, filed on Sep. 7, 2018.

(51) Int. Cl.
*A61B 1/00* (2006.01)

(52) U.S. Cl.
CPC ...... *A61B 1/00188* (2013.01); *A61B 1/00009* (2013.01)

(58) Field of Classification Search
CPC ... A61B 1/00188; A61B 1/00163; A61B 1/04; G02B 23/243; G02B 15/143505; G02B 15/144109
USPC .......................................................... 600/167
See application file for complete search history.

(56) References Cited

U.S. PATENT DOCUMENTS

| 4,558,928 | A |   | 12/1985 | Imaizumi |               |
|-----------|---|---|---------|----------|---------------|
| 4,948,234 | A | * | 8/1990  | Mihara   | G02B 15/144109|
|           |   |   |         |          | 359/688       |
| 5,117,309 | A | * | 5/1992  | Aoki     | G02B 15/143103|
|           |   |   |         |          | 359/689       |

(Continued)

FOREIGN PATENT DOCUMENTS

| JP | S59116709 A | 7/1984  |
|----|-------------|---------|
| JP | H06289291 A | 10/1994 |

(Continued)

OTHER PUBLICATIONS

Japanese Office Action (and English language translation thereof) dated Nov. 4, 2021, issued in counterpart Japanese Application No. 2020-540976.

(Continued)

*Primary Examiner* — Ryan N Henderson
*Assistant Examiner* — Pamela F Wu
(74) *Attorney, Agent, or Firm* — Holtz, Holtz & Volek PC

(57) ABSTRACT

An objective optical system includes, in order from an object side: a positive first group; a negative second group; a negative third group; and a positive fourth group, in which the second group and the third group move together toward an image side to perform focusing from an object point at a long distance to an object point at a close distance, and the following conditional expression (2) is satisfied: $0.2<(t34f-t34n)/F<2$ (2), where t34f is a distance between the third group and the fourth group at a time of focusing to the object point at the long distance, t34n is a distance between the third group and the fourth group at a time of focusing to the object point at the close distance, and F is a focal length of the overall objective optical system at a time of focusing to the object point at the long distance.

4 Claims, 17 Drawing Sheets

(56) References Cited

U.S. PATENT DOCUMENTS

| | | | |
|---|---|---|---|
| 5,909,319 A | 6/1999 | Matsui | |
| 6,046,861 A * | 4/2000 | Steele | G02B 15/144109 359/688 |
| 6,353,504 B1 | 3/2002 | Yamamoto | |
| 7,511,892 B2 | 3/2009 | Takato | |
| 7,889,434 B2 * | 2/2011 | Pauker | A61B 1/00096 359/666 |
| 8,164,836 B2 | 4/2012 | Uzawa et al. | |
| 8,922,916 B2 | 12/2014 | Yamamoto et al. | |
| 8,947,785 B2 | 2/2015 | Yamamoto | |
| 9,019,621 B2 | 4/2015 | Takada et al. | |
| 9,645,382 B2 | 5/2017 | Yamamoto | |
| 2007/0258150 A1 * | 11/2007 | Takato | G02B 13/006 359/686 |
| 2011/0235192 A1 | 9/2011 | Uzawa et al. | |
| 2011/0317284 A1 * | 12/2011 | Imamura | G02B 15/145125 359/745 |
| 2013/0163094 A1 | 6/2013 | Takada et al. | |
| 2014/0218811 A1 | 8/2014 | Yamamoto | |
| 2014/0240855 A1 | 8/2014 | Yamamoto et al. | |
| 2015/0022907 A1 | 1/2015 | Yamamoto | |

FOREIGN PATENT DOCUMENTS

| | | |
|---|---|---|
| JP | H10104505 A | 4/1998 |
| JP | 2002072089 A | 3/2002 |
| JP | 3722458 B2 | 11/2005 |
| JP | 2007260305 A | 10/2007 |
| JP | 2009300489 A | 12/2009 |
| JP | 4723628 B2 | 7/2011 |
| JP | 4834799 B2 | 12/2011 |
| JP | 2013104956 A | 5/2013 |
| JP | 5567224 B2 | 8/2014 |
| JP | 5567225 B2 | 8/2014 |
| JP | 2015022161 A | 2/2015 |

OTHER PUBLICATIONS

International Preliminary Report on Patentability (IPRP) (and English language translation thereof) dated Mar. 18, 2021 issued in International Application No. PCT/JP2018/033232.

International Search Report (ISR) (and English language translation thereof) dated Dec. 11, 2018, issued in International Application No. PCT/JP2018/033232.

Written Opinion dated Dec. 11, 2018, issued in International Application No. PCT/JP2018/033232.

* cited by examiner

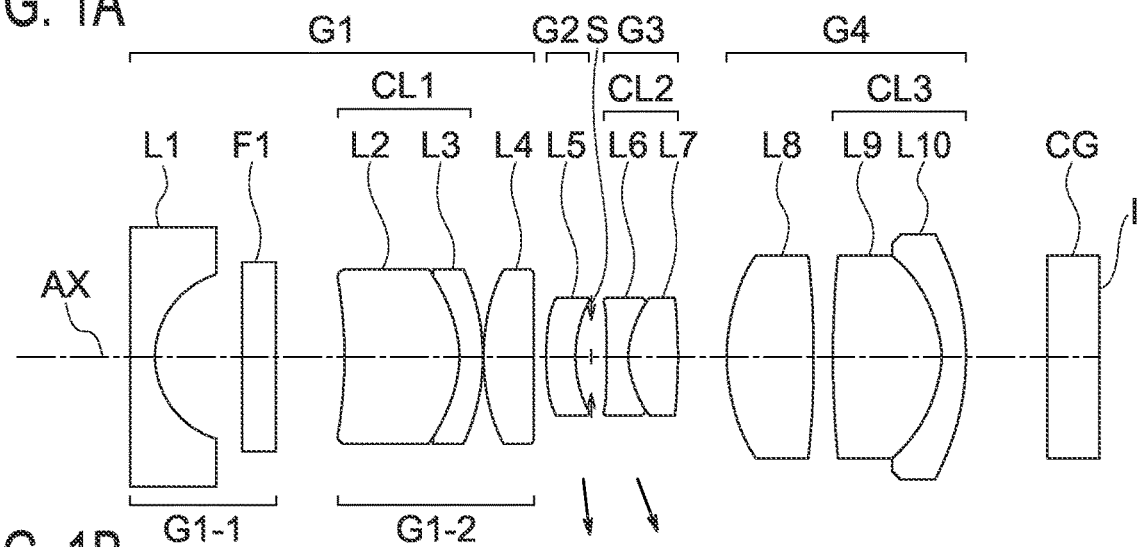
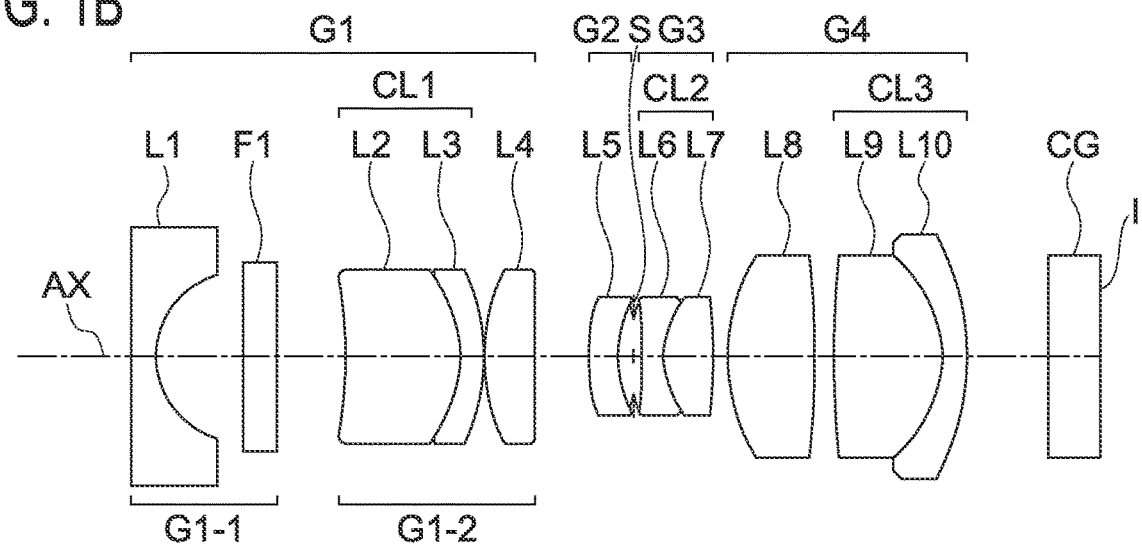

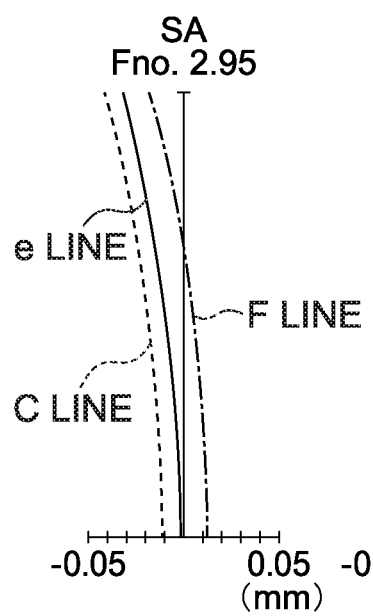
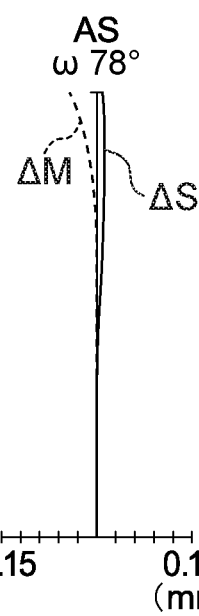
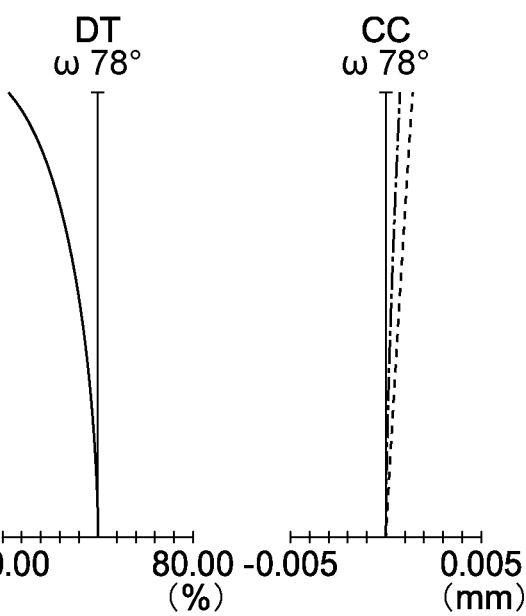
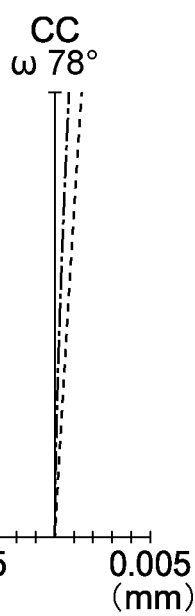
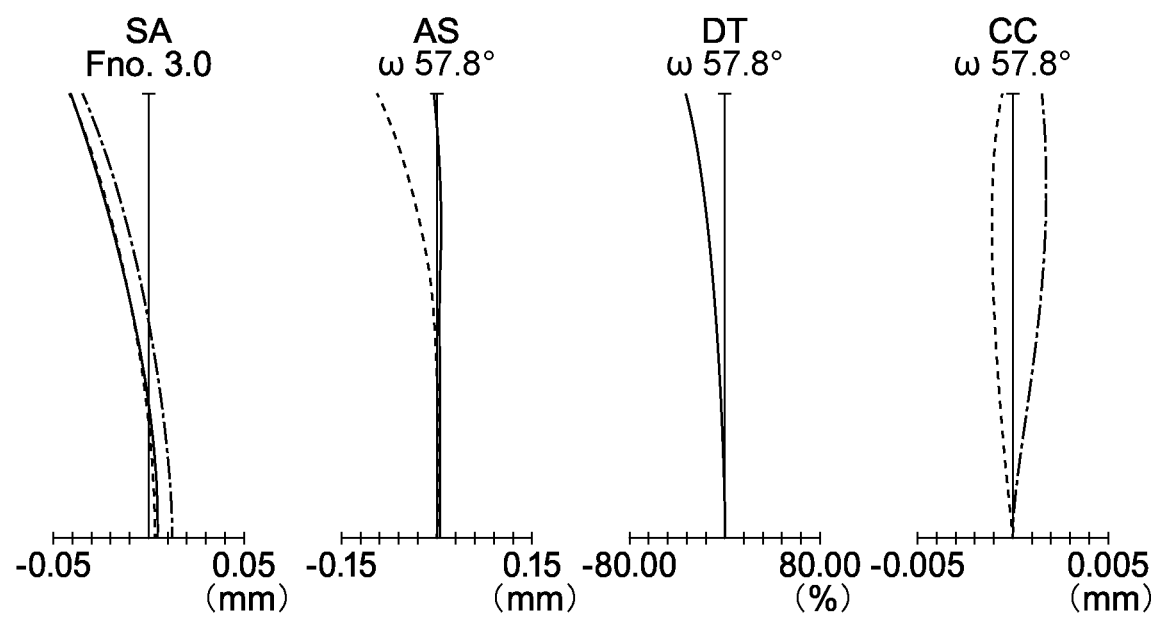

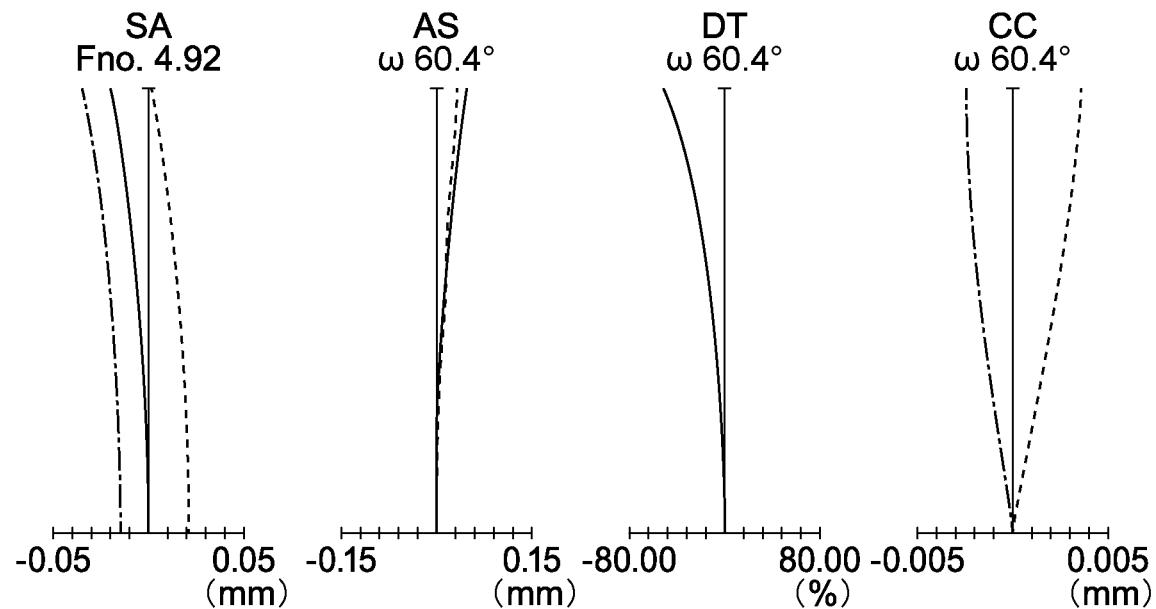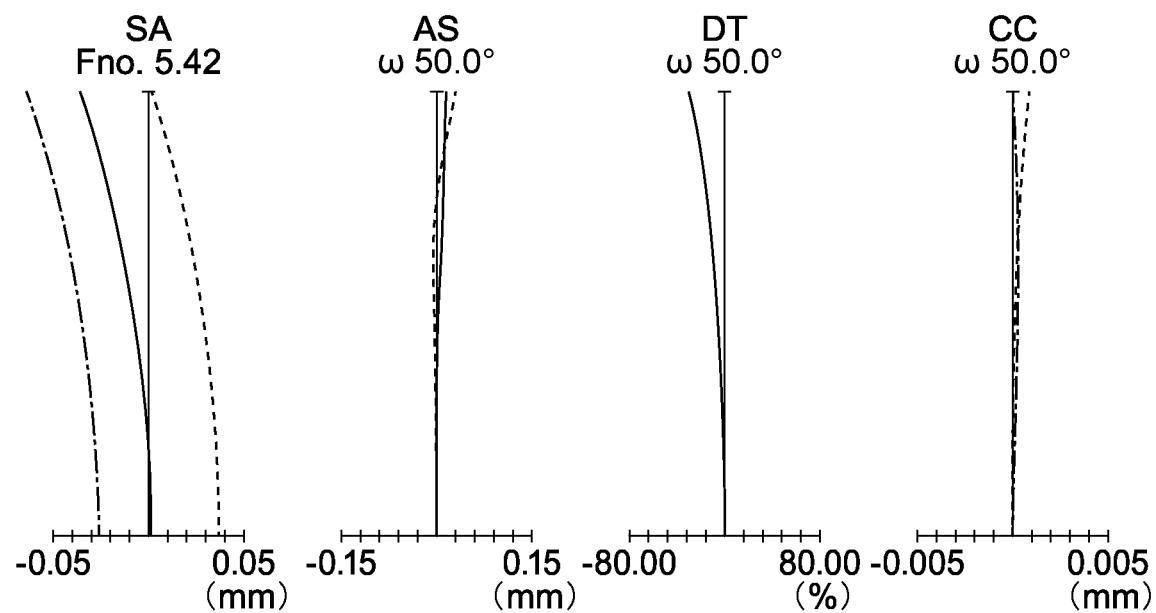

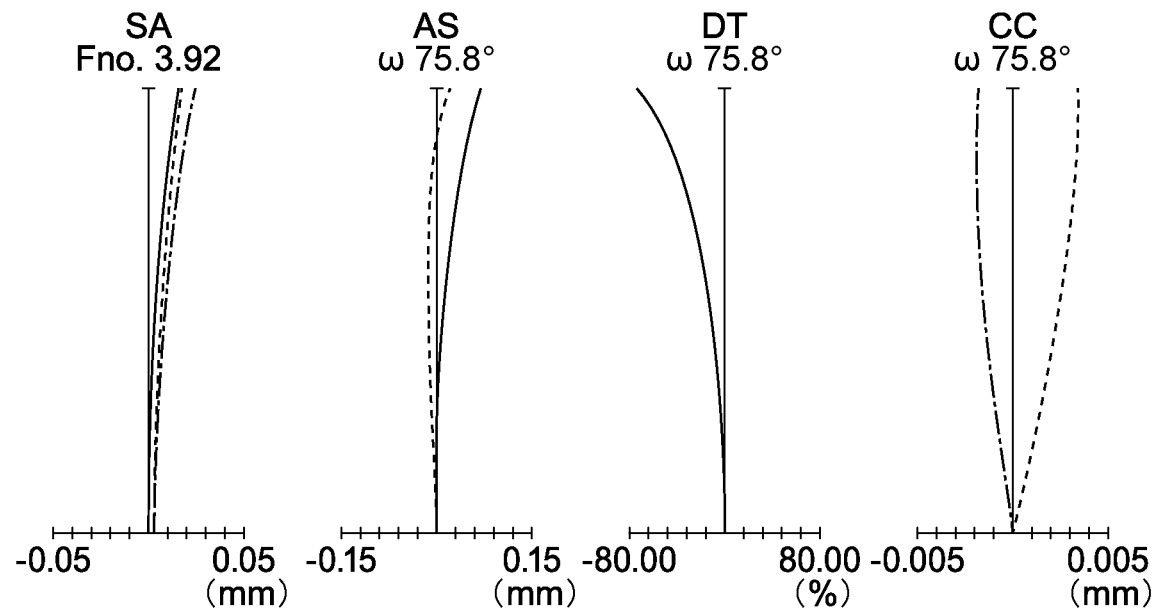
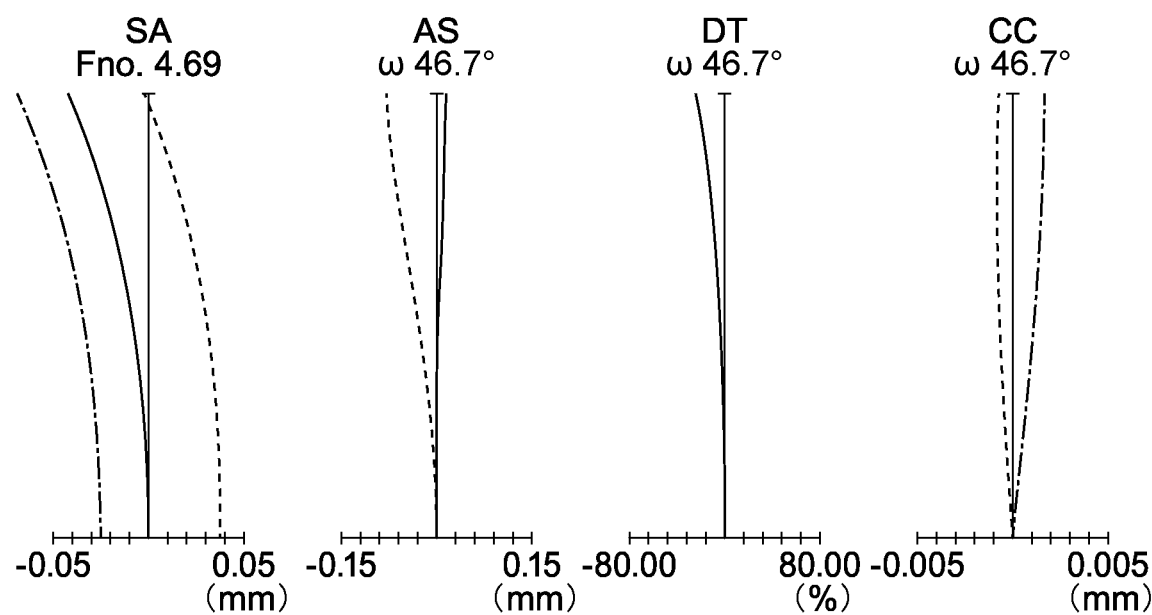

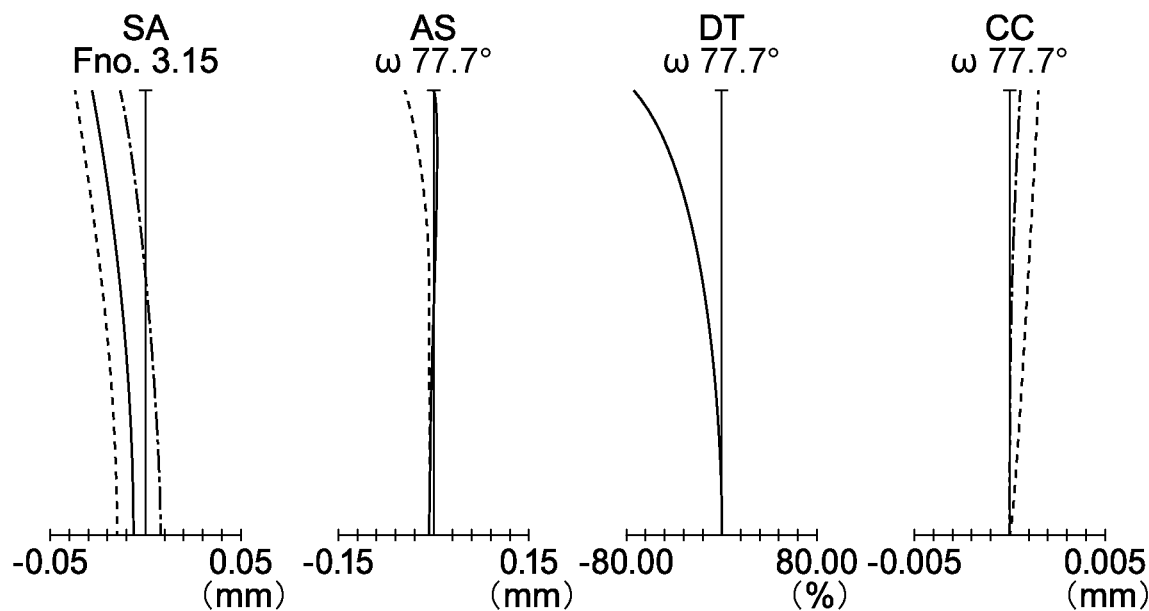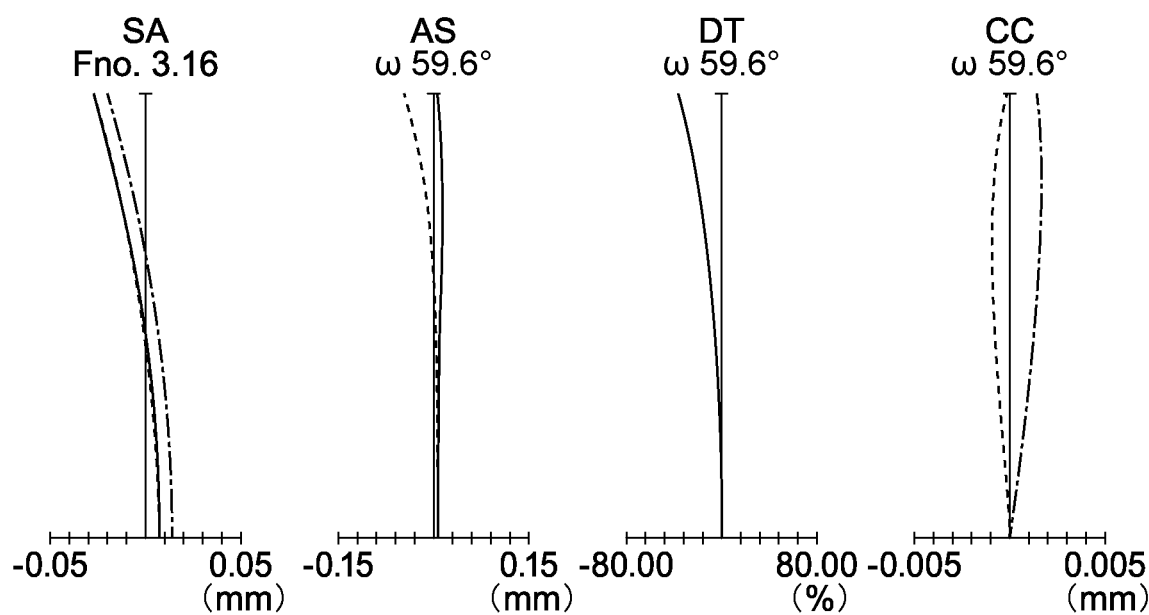

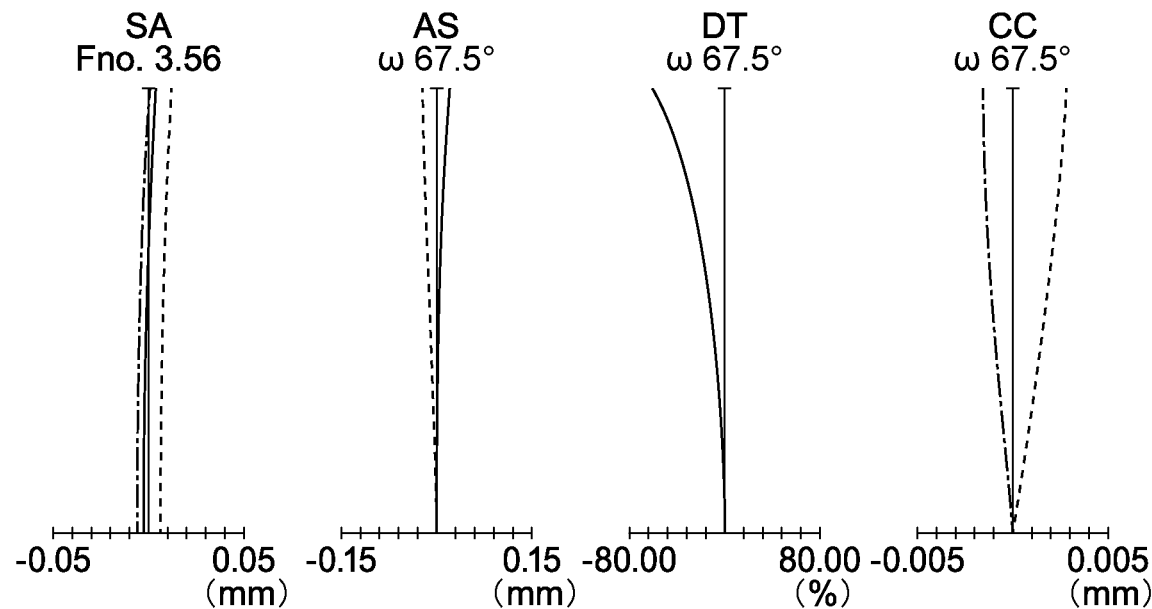
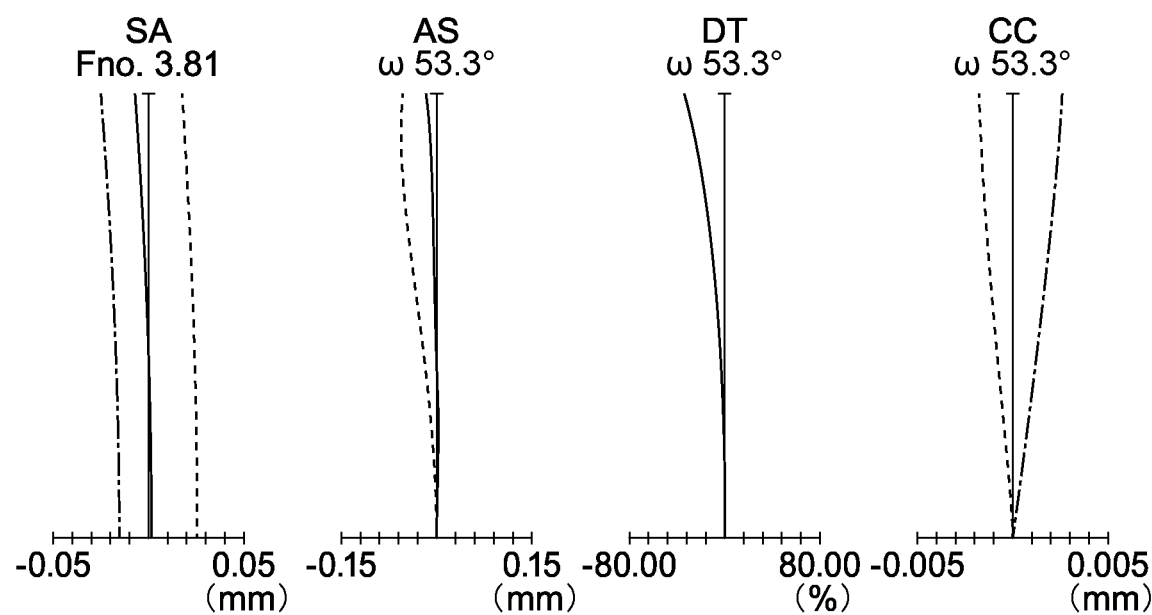

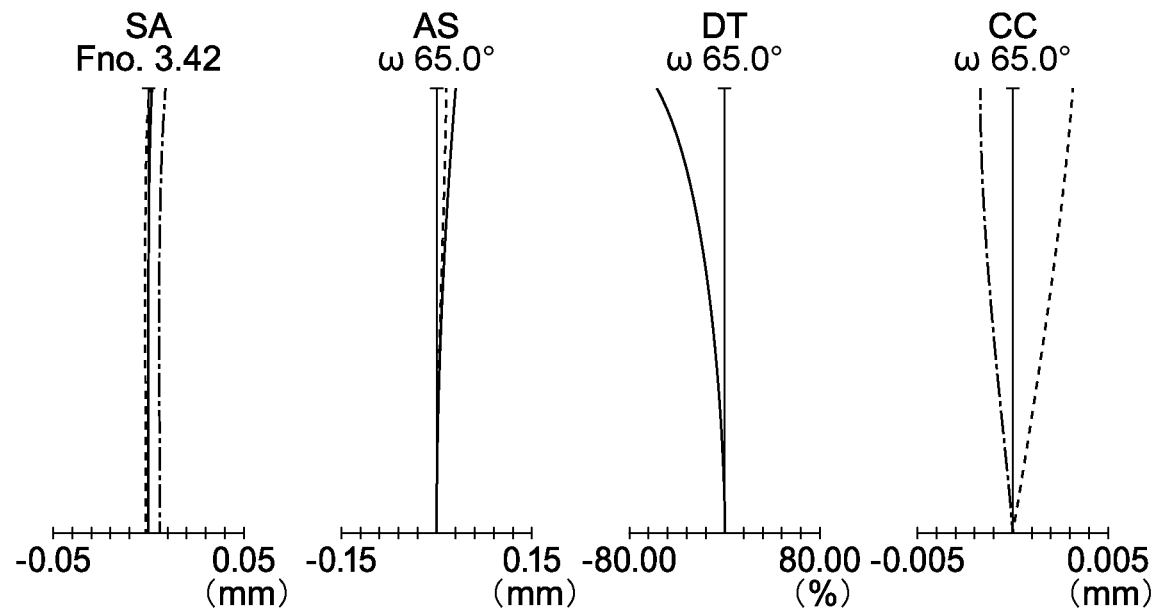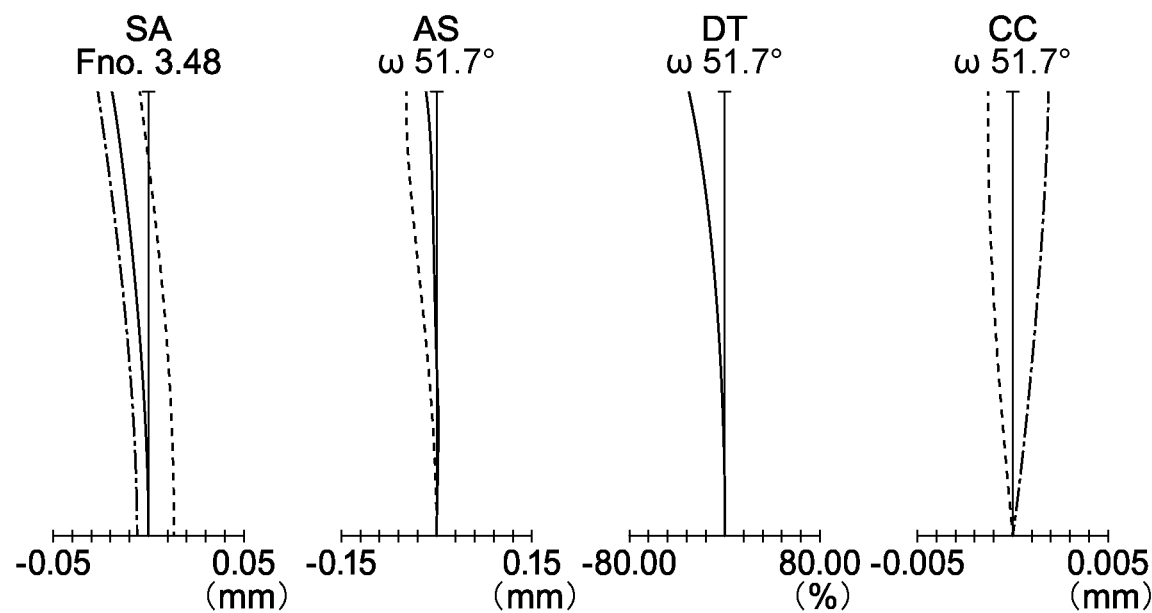

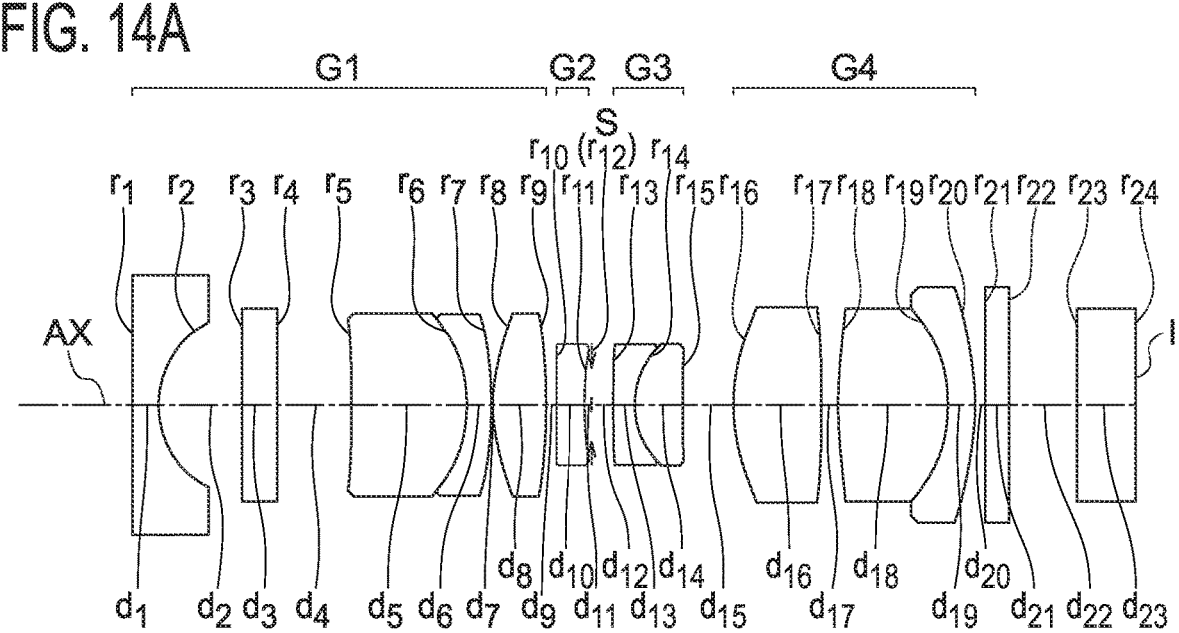
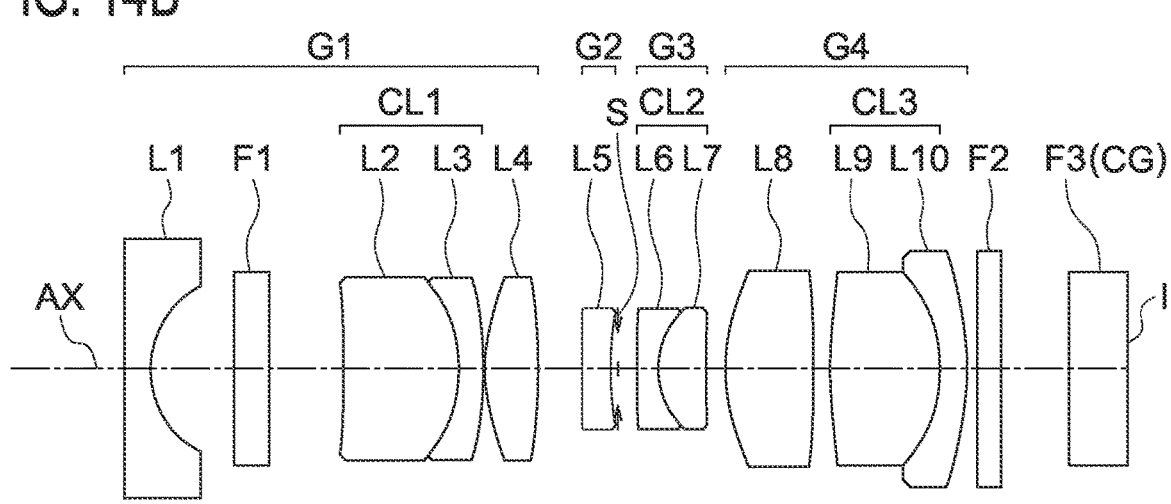

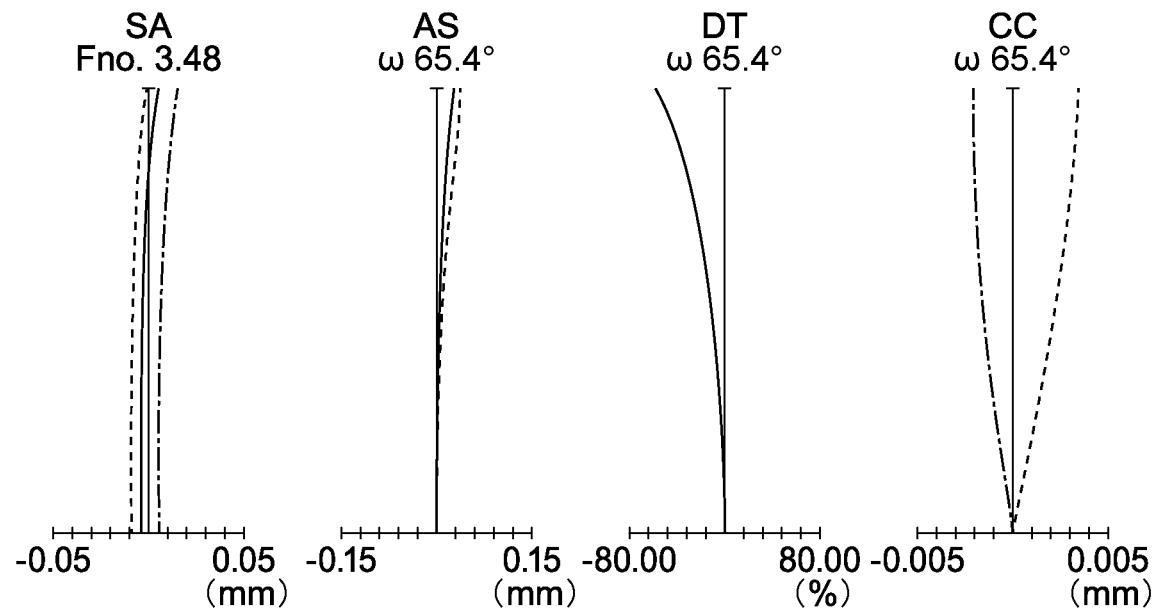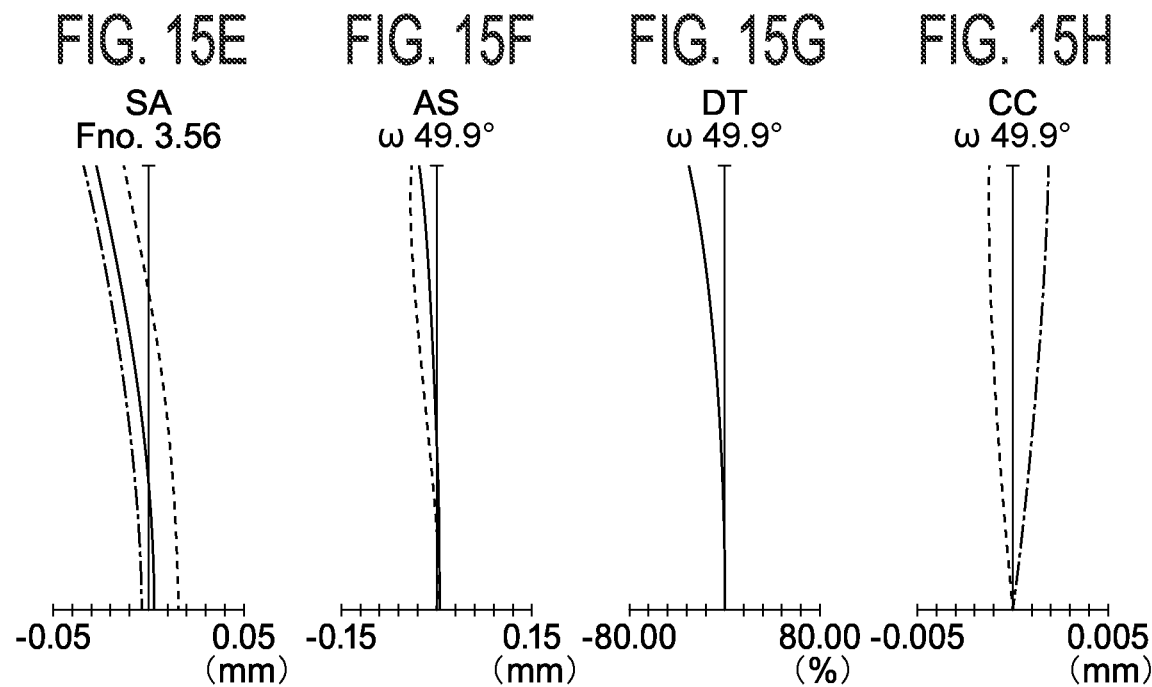

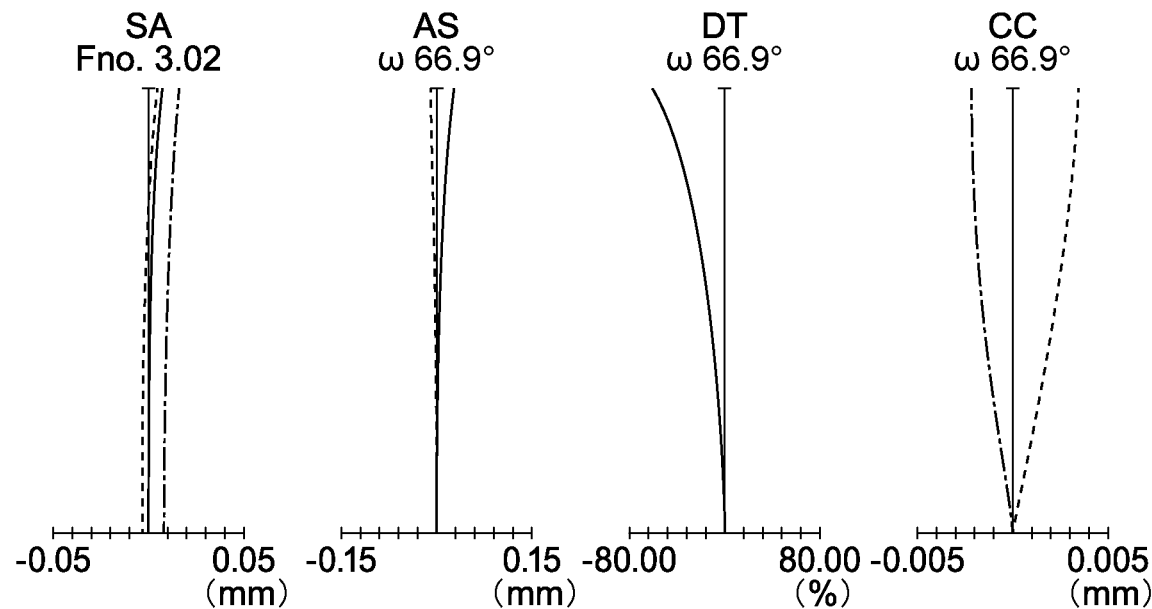
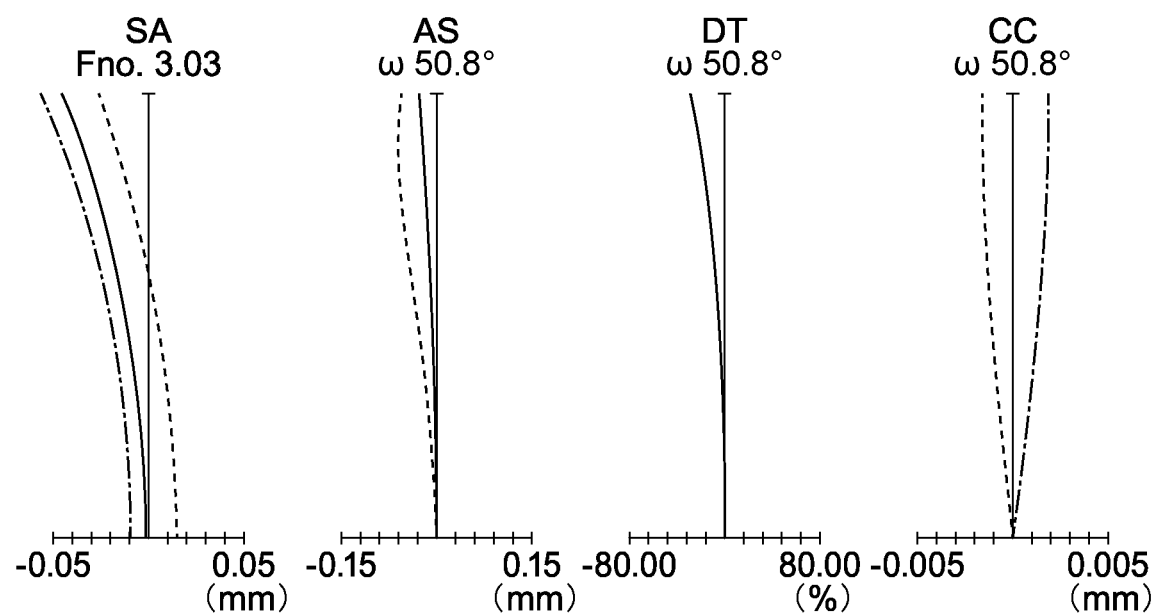

OBJECTIVE OPTICAL SYSTEM AND ENDOSCOPE USING THE SAME

CROSS-REFERENCE TO RELATED APPLICATION

The present application is a continuation application of PCT/JP2018/033232 filed on Sep. 7, 2018; the entire contents of which are incorporated herein by reference.

BACKGROUND

Technical Field

The disclosure relates to an objective optical system having a focusing function and an endoscope using the same. Specifically, the disclosure relates to photographic lenses for endoscope objective optical systems capable of close observation and other compact cameras for consumer use.

Description of the Related Art

Common endoscope objective optical systems have a depth of field in a wide range of about 5 mm to 100 mm on the object side. In an endoscope equipped with such an objective optical system, images are provided using a solid-state image sensor such as a CCD and a CMOS. In recent years, higher image quality of endoscopic images has been sought for the purpose of improving accuracy in diagnosis. For higher image quality of endoscopic images, image sensors have higher and higher resolution.

However, when a high-definition image sensor is used, image quality is degraded due to diffraction. In order to avoid degradation in image quality, it is necessary to reduce the F number (Fno) of the objective optical system. Moreover, the size of the image sensor is increased as a consequence of increase in pixel count. When the size of the image sensor is increased, the focal length of the objective optical system also needs to be increased. Because of reducing the Fno and increasing the focal length of the objective optical system, the depth of field becomes narrow. Therefore, there is an increasing need for objective optical systems having a focusing function in order to ensure the depth of field comparable to the conventional one.

Furthermore, in recent years, in the field of medical endoscopes, there has been a growing demand for optical systems capable of magnified observation (close observation) in order to carry out qualitative diagnosis of lesions. An endoscope objective optical system capable of magnified observation focuses to a subject distance of approximately 1 mm to 3 mm to enable magnified observation.

In objective optical systems for magnifying endoscopes capable of focusing to an object point at a close distance, many optical systems of the type having one movable group are disclosed. Furthermore, in objective optical systems for magnifying endoscopes, objective optical systems for magnifying endoscopes with two movable groups are disclosed in Japanese Patent No. 4723628, Japanese Patent No. 3722458, Japanese Patent Application Laid-open No. 2009-300489, Japanese Patent No. 4834799, Japanese Patent Application Laid-open No. 2015-22161, Japanese Patent No. 5567224, Japanese Patent No. 5567225, Japanese Patent Application Laid-open No. H06-289291, and Japanese Patent Application Laid-open No. 2002-72089.

SUMMARY

An objective optical system according to at least some embodiments of the present disclosure includes, in order from an object side: a positive first group; a negative second group; a negative third group; and a positive fourth group, in which the second group and the third group move together toward an image side to perform focusing from an object point at a long distance to an object point at a close distance, and the conditional expression (2) is satisfied:

$$0.2 < (t34f - t34n)/F < 2 \qquad (2)$$

where
t34f is a distance between the third group and the fourth group at a time of focusing to the object point at the long distance,
t34n is a distance between the third group and the fourth group at a time of focusing to the object point at the close distance, and
F is a focal length of the overall objective optical system at a time of focusing to the object point at the long distance.

Hereinafter "normal observation state" is referred to as at a time of focusing to the object point at the long distance, if necessary. Furthermore, "magnified observation state" is referred to as a close observation state or at a time of focusing to the object point at the close distance, if necessary.

An endoscope according to at least some embodiments of the present disclosure uses the objective optical system described above.

BRIEF DESCRIPTION OF THE DRAWINGS

FIG. 1A and FIG. 1B are diagrams illustrating a sectional configuration of an objective optical system according to an embodiment of the present disclosure, in which FIG. 1A is a sectional view in a normal observation state of the objective optical system, and FIG. 1B is a sectional view in a close observation state of the objective optical system;

FIG. 2A and FIG. 2B are diagrams illustrating a sectional configuration of an objective optical system according to Example 1 of the present disclosure, in which FIG. 2A is a sectional view in a normal observation state of the objective optical system, and FIG. 2B is a sectional view in a close observation state of the objective optical system;

FIG. 3A, FIG. 3B, FIG. 3C, and FIG. 3D are aberration diagrams illustrating spherical aberration (SA), astigmatism (AS), distortion (DT), and chromatic aberration of magnification (CC), respectively, in the normal observation state of the objective optical system according to Example 1, and FIG. 3E, FIG. 3F, FIG. 3G, and FIG. 3H are aberration diagrams illustrating spherical aberration (SA), astigmatism (AS), distortion (DT), and chromatic aberration of magnification (CC), respectively, in the close observation state of the objective optical system according to Example 1;

FIG. 4A and FIG. 4B are diagrams illustrating a sectional configuration of an objective optical system according to Example 2 of the present disclosure, in which FIG. 4A is a sectional view in a normal observation state of the objective optical system, and FIG. 4B is a sectional view in a close observation state of the objective optical system;

FIG. 5A, FIG. 5B, FIG. 5C, and FIG. 5D are aberration diagrams illustrating spherical aberration (SA), astigmatism (AS), distortion (DT), and chromatic aberration of magnification (CC), respectively, in the normal observation state of the objective optical system according to Example 2, and FIG. 5E, FIG. 5F, FIG. 5G, and FIG. 5H are aberration diagrams illustrating spherical aberration (SA), astigmatism (AS), distortion (DT), and chromatic aberration of magnification (CC), respectively, in the close observation state of the objective optical system according to Example 2;

FIG. 6A and FIG. 6B are diagrams illustrating a sectional configuration of an objective optical system according to Example 3 of the present disclosure, in which FIG. 6A is a sectional view in a normal observation state, and FIG. 6B is a sectional view in a close observation state;

FIG. 7A, FIG. 7B, FIG. 7C, and FIG. 7D are aberration diagrams illustrating spherical aberration (SA), astigmatism (AS), distortion (DT), and chromatic aberration of magnification (CC), respectively, in the normal observation state of the objective optical system according to Example 3, and FIG. 7E, FIG. 7F, FIG. 7G, and FIG. 7H are aberration diagrams illustrating spherical aberration (SA), astigmatism (AS), distortion (DT), and chromatic aberration of magnification (CC), respectively, in the close observation state of the objective optical system according to Example 3;

FIG. 8A and FIG. 8B are diagrams illustrating a sectional configuration of an objective optical system according to Example 4 of the present disclosure, in which FIG. 8A is a sectional view in a normal observation state, and FIG. 8B is a sectional view in a close observation state;

FIG. 9A, FIG. 9B, FIG. 9C, and FIG. 9D are aberration diagrams illustrating spherical aberration (SA), astigmatism (AS), distortion (DT), and chromatic aberration of magnification (CC), respectively, in the normal observation state of the objective optical system according to Example 4, and FIG. 9E, FIG. 9F, FIG. 9G, and FIG. 9H are aberration diagrams illustrating spherical aberration (SA), astigmatism (AS), distortion (DT), and chromatic aberration of magnification (CC), respectively, in the close observation state of the objective optical system according to Example 4;

FIG. 10A and FIG. 10B are diagrams illustrating a sectional configuration of an objective optical system according to Example 5 of the present disclosure, in which FIG. 10A is a sectional view in a normal observation state, and FIG. 10B is a sectional view in a close observation state;

FIG. 11A, FIG. 11B, FIG. 11C, and FIG. 11D are aberration diagrams illustrating spherical aberration (SA), astigmatism (AS), distortion (DT), and chromatic aberration of magnification (CC), respectively, in the normal observation state of the objective optical system according to Example 5, and FIG. 11E, FIG. 11F, FIG. 11G, and FIG. 11H are aberration diagrams illustrating spherical aberration (SA), astigmatism (AS), distortion (DT), and chromatic aberration of magnification (CC), respectively, in the close observation state of the objective optical system according to Example 5;

FIG. 12A and FIG. 12B are diagrams illustrating a sectional configuration of an objective optical system according to Example 6 of the present disclosure, in which FIG. 12A is a sectional view in a normal observation state, and FIG. 12B is a sectional view in a close observation state;

FIG. 13A, FIG. 13B, FIG. 13C, and FIG. 13D are aberration diagrams illustrating spherical aberration (SA), astigmatism (AS), distortion (DT), and chromatic aberration of magnification (CC), respectively, in the normal observation state of the objective optical system according to Example 6, and FIG. 13E, FIG. 13F, FIG. 13G, and FIG. 13H are aberration diagrams illustrating spherical aberration (SA), astigmatism (AS), distortion (DT), and chromatic aberration of magnification (CC), respectively, in the close observation state of the objective optical system according to Example 6;

FIG. 14A and FIG. 14B are diagrams illustrating a sectional configuration of an objective optical system according to Example 7 of the present disclosure, in which FIG. 14A is a sectional view in a normal observation state, and FIG. 14B is a sectional view in a close observation state;

FIG. 15A, FIG. 15B, FIG. 15C, and FIG. 15D are aberration diagrams illustrating spherical aberration (SA), astigmatism (AS), distortion (DT), and chromatic aberration of magnification (CC), respectively, in the normal observation state of the objective optical system according to Example 7, and FIG. 15E, FIG. 15F, FIG. 15G, and FIG. 15H are aberration diagrams illustrating spherical aberration (SA), astigmatism (AS), distortion (DT), and chromatic aberration of magnification (CC), respectively, in the normal observation state of the objective optical system according to Example 7;

FIG. 16A and FIG. 16B are diagrams illustrating a sectional configuration of an objective optical system according to Example 8 of the present disclosure, in which FIG. 16A is a sectional view in a normal observation state, and FIG. 16B is a sectional view in a close observation state; and FIG. 17A, FIG. 17B, FIG. 17C, and FIG. 17D are aberration diagrams illustrating spherical aberration (SA), astigmatism (AS), distortion (DT), and chromatic aberration of magnification (CC), respectively, in the normal observation state of the objective optical system according to Example 8, and FIG. 17E, FIG. 17F, FIG. 17G, and FIG. 17H are aberration diagrams illustrating spherical aberration (SA), astigmatism (AS), distortion (DT), and chromatic aberration of magnification (CC), respectively, in the close observation state of the objective optical system according to Example 8.

DETAILED DESCRIPTION

Figure 2A:
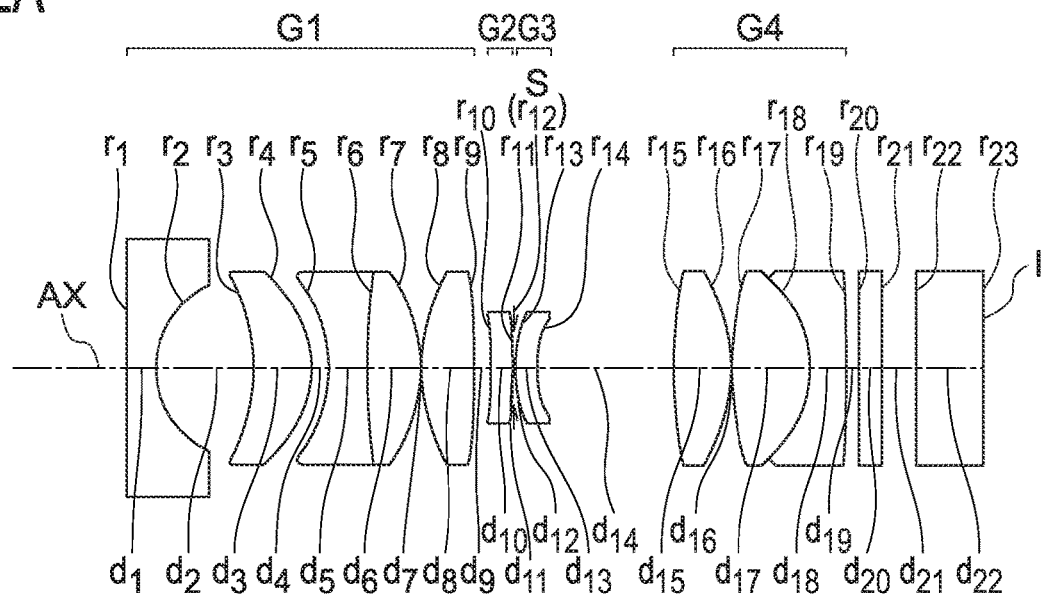

An objective optical system and an endoscope using the same according to an embodiment will be explained in detail below in conjunction with the drawings. It should be noted that the present disclosure is not limited by the embodiment.

FIG. 1A and FIG. 1B are diagrams illustrating a sectional configuration of an objective optical system according to an embodiment of the present disclosure. FIG. 1A is a sectional view in a normal observation state of the objective optical system, and FIG. 1B is a sectional view in a close observation state of the objective optical system.

The objective optical system according to the present embodiment includes, in order from an object side: a first group G1 having a positive refractive power; a second group G2 having a negative refractive power; an aperture stop S; a third group G3 having a negative refractive power; and a fourth group G4 having a positive refractive power.

The positive first group G1 includes, in order from the object side: a negative first lens L1; a positive second lens L2; a negative third lens L3; and a positive fourth lens L4. The positive second lens L2 and the negative third lens L3 are cemented to form a cemented lens CL1.

The negative second group G2 includes a negative fifth lens L5.

The negative third group G3 includes, in order from the object side: a negative sixth lens L6; and a positive seventh lens L7. The negative sixth lens L6 and the positive seventh lens L7 are cemented to form a cemented lens CL2.

The second group G2 moves toward an image side, and the third group G3 moves together toward the image side. Thus, focusing from an object point at a long distance to an object point at a close distance is achieved.

The positive fourth group G4 includes, in order from the object side: a positive eighth lens L8; a positive ninth lens L9; and a negative tenth lens L10. The positive ninth lens L9 and the negative tenth lens L10 are cemented to form a cemented lens CL3.

The aperture stop S is disposed between the second group G2 and the third group G3.

A first parallel plate F1 is disposed between the negative first lens L1 and the positive second lens L2. It is possible to dispose the first parallel plate F1 at any position in the objective optical system. Furthermore, an image pickup surface (image plane I) of an image sensor (not illustrate) is disposed at an image plane I of the objective optical system. A cover glass CG that is a parallel plate is fixed to the image pickup surface.

The configuration of the objective optical system of the present embodiment will be explained below.

Furthermore, according to a preferable aspect of the present embodiment, in the optical system using movable groups, the moving distance of each lens group is important in order to achieve size reduction and higher performance. Therefore, it is desirable that the objective optical system according to the present embodiment satisfy the following conditional expression (1):

$$0.1 < (t12n - t12f)/F < 1.2 \quad (1)$$

where
t12n is a distance between the first group G1 and the second group G2 at a time of focusing to the object point at the close distance,
t12f is a distance between the first group G1 and the second group G2 at a time of focusing to the object point at the long distance, and
F is the focal length of the overall objective optical system at a time of focusing to the object point at the long distance. Here, the distance between the first group G1 and the second group G2 is the distance between a lens surface of the first group G1 nearest to the image plane and a lens surface of the second lens group G2 nearest to the object.

Furthermore, according to a preferable aspect of the present embodiment, it is desirable that the following conditional expression (2) be satisfied:

$$0.2 < (t34f - t34n)/F < 2 \quad (2)$$

where
t34f is a distance between the third group G3 and the fourth group G4 at a time of focusing to the object point at the long distance,
t34n is a distance between the third group G3 and the fourth group G4 at a time of focusing to the object point at the close distance, and
F is the focal length of the overall objective optical system at a time of focusing to the object point at the long distance. Here, the distance between the third group G3 and the fourth group G4 is the distance between a lens surface of the third group G3 nearest to the image plane and a lens surface of the fourth lens group G4 nearest to the object.

The conditional expression (1) and conditional expression (2) relate to the moving distance of lens in each of the second group G2 and the third group G3.

When the conditional expression (1) takes a value smaller than the lower limit value thereof, it is difficult to ensure the moving distance of the second group G2. Furthermore, when the conditional expression (1) takes a value larger than the upper limit value thereof, the distance between the first group G1 and the second group G2 becomes excessively large. Therefore, it is possible to ensure the moving distance of the second group G2. However, since the overall length of the optical system becomes excessively long, the size of the optical system may be increased.

It is preferable that the following conditional expression (1') be satisfied instead of the conditional expression (1).

$$0.1 < (t12n - t12f)/F < 0.7 \quad (1')$$

Accordingly, it is possible to further reduce the size of the objective optical system.

The conditional expression (2) contributes to ensuring the moving distance of the movable group and size reduction, in the same manner as the conditional expression (1). When the conditional expression (2) takes a value smaller than the lower limit value thereof, it is difficult to ensure the moving distance of the third group G3. Furthermore, when the conditional expression (2) takes a value larger than the upper limit value thereof, the distance between the third group G3 and the fourth group G4 becomes excessively large. Thus, it is possible to ensure the moving distance of the third group G3. However, since the overall length of the objective optical system becomes excessively long, the size of the optical system may be increased.

For size reduction of the overall length of the objective optical system, it is desirable that the upper limit value of the conditional expression (2) be limited to the following range.

It is preferable that the following conditional expression (2') be satisfied instead of the conditional expression (2).

$$0.2 < (t34f - t34n)/F < 1.6 \quad (2')$$

Accordingly, it is possible to further reduce the size of the objective optical system.

It is more preferable that the following conditional expression (2") be satisfied instead of the conditional expression (2).

$$0.2 < (t34f - t34n)/F < 1.2 \quad (2'')$$

Accordingly, it is possible to even further reduce the size of the objective optical system.

Furthermore, according to a preferable aspect of the present embodiment, as for the moving distance of the movable group, it is desirable that the following conditional expression (3) be satisfied, together with the conditional expression (1) and the conditional expression (2):

$$0.1 < (t12n - t12f)/(t34f - t34n) < 2.2 \quad (3)$$

where
t12n is the distance between the first group G1 and the second group G2 at a time of focusing to the object point at the close distance,
t12f is the distance between the first group G1 and the second group G2 at a time of focusing to the object point at the long distance,
t34f is the distance between the third group G3 and the fourth group G4 at a time of focusing to the object point at the long distance, and
t34n is the distance between the third group G3 and the fourth group G4 at a time of focusing to the object point at the close distance.

The conditional expression (3) relates to an appropriate range of the moving distance of the movable group. When the conditional expression (3) takes a value smaller than the lower limit value thereof, the distance between the first group G1 and the second group G2 becomes small. In this case, it is difficult to ensure the space in which the second group G2 is moved.

One of the features of the objective optical system of the present embodiment is that it is possible to focus to a nearest object point distance of around 3 mm. At a time of focusing, when it is impossible to ensure the moving distance of a lens, it is impossible to focus to the object point at the close distance. Therefore, observation with a sufficient magnification becomes difficult as for the object point at the close distance.

Moreover, when the moving distance of the second group G2 is reduced so as to be fitted in a predetermined space, image plane position sensitivity by position accuracy on the optical axis of the second group G2 becomes higher. In this case, inconvenience such as increase in image plane displacement for displacement of the second group G2 due to a manufacturing error is likely to occur.

Furthermore, when the conditional expression (3) takes a value larger than the upper limit value thereof, the distance between the third group G3 and the fourth group G4 becomes small. In this case, it is difficult to ensure a movement space for the third group G3. At a time of focusing, when it is impossible to ensure the moving distance of a lens, it is impossible to focus to the object point at the close distance. Therefore, observation with a sufficient magnification is difficult as for the object point at the close distance.

Moreover, when the moving distance of the third group G3 is reduced so as to be fitted in an insufficient space, image plane position sensitivity by position accuracy on the optical axis of the third group G3 becomes higher. In this case, inconvenience such as increase in image plane displacement for position displacement of the third group G3 due to a manufacturing error is likely to occur.

It is preferable that the following conditional expression (3') be satisfied instead of the conditional expression (3).

$$0.1 < (t12n - t12f)/(t34f - t34n) < 1.6 \quad (3')$$

Accordingly, it becomes further easier to ensure the movement space for the third group G3.

Furthermore, according to a preferable aspect of the present embodiment, the first group G1 includes, in order from the object side: the negative first lens L1; and the subsequent positive sub-lens group. The subsequent positive sub-lens group refers to the subsequent lenses on the image plane side of the first group G1. Specifically, the subsequent positive sub-lens group is lenses on the rear side (image plane side) of the second lens L2. Therefore, the subsequent positive sub-lens group refers to from the second lens L2 to the last fourth lens L4 in the first group G1. The parallel plate F1 does not have a refractive power. Therefore, the parallel plate F1 may be or may not be included in the first group G1. In the present embodiment, the lens nearest to the object in the first group G1 includes the parallel plate F1.

It is desirable that the negative first lens L1 be a flat concave lens having a concave surface directed toward the image side. The distal end of the endoscope has a mechanism of feeding water. This mechanism feeds water for washing a lens surface from a nozzle. When the distal end of the objective optical system is a flat surface, it is easy to feed water to and washes a position far from a water feeding part of the nozzle on the opposite side to the water feeding part of the nozzle.

It is preferable that the subsequent positive sub-lens group at least include the positive fourth lens L4 and the cemented lens CL1. In this way, the first group G1 has a negative and positive refractive power configuration. Furthermore, the negative refractive power of the first lens L1 and the refractive power of the subsequent positive sub-lens group in the first group G1 are arranged appropriately. Accordingly, it becomes easy to ensure the movement space for the second group G2 and the third group G3. Furthermore, it is possible to achieve a balance of correction between longitudinal chromatic aberration and chromatic aberration of magnification. In addition, it is possible to favorably correct curvature of field.

Furthermore, according to a preferable aspect of the present embodiment, it is desirable that the following conditional expression (4) be satisfied:

$$-1 < fG1-1/F < -2 \quad (4)$$

where
fG1-1 is the focal length of a lens nearest to the object in the first group G1, and
F is the focal length of the overall objective optical system at a time of focusing to the object point at the long distance.

The conditional expression (4) relates to correction of variation in curvature of field due to change in object point distance. Falling below the lower limit value of the conditional expression (4) is not preferable because if so, the curvature of field at a time of focusing to the object point at the close distance is greatly inclined toward the over side. Furthermore, when a value is larger than the upper limit value of the conditional expression (4), the curvature of field at a time of focusing to the object point at the long distance is greatly inclined toward the under side and, in addition, coma correction becomes difficult. Moreover, since it becomes difficult to ensure a back focus in the first group G1, it becomes difficult to ensure a space for the movable group on the rear side.

Furthermore, according to a preferable aspect of the present embodiment, it is desirable that the following conditional expression (5) be satisfied:

$$1.8 < fG1-2/F < 3.5 \quad (5)$$

where
fG1-2 is the focal length of the positive sub-lens group subsequent to the lens nearest to the object in the first group G1, and
F is the focal length of the overall objective optical system at a time of focusing to the object point at the long distance.

The conditional expression (5) relates to an appropriate ratio of fG1-2 and F. When the conditional expression (5) takes a value smaller than the lower limit value thereof, the refractive power in the subsequent positive sub-lens group is too large and therefore it becomes difficult to ensure a movable space after the second group G2. Furthermore, the image plane is inclined toward the under side when the object point at the close distance is observed. Thus, the curvature of field becomes large.

When the conditional expression (5) takes a value larger than the upper limit value thereof, for both longitudinal chromatic aberration and chromatic aberration of magnification, the aberration curve of C line (656.3 nm) is inclined toward the under side, and the aberration curve of F line (486.1 nm) is inclined toward the over side. Thus, it becomes difficult to correct chromatic aberration.

It is preferable that the following conditional expression (5') be satisfied instead of the conditional expression (5).

$$2 < fG1-2/F < 3 \quad (5')$$

Within a range that satisfies the conditional expression (5'), curvature of field correction is easy and, in addition, it is also possible to correct chromatic aberration more favorably.

Furthermore, according to a preferable aspect of the present embodiment, it is desirable that the refractive power of the positive first group G1 be arranged appropriately. Chromatic aberration that occurs in the first group G1 is corrected favorably. In this case, even when chromatic aberration occurs in a subsequent group, the aberration is corrected sufficiently within a range of the following conditional expression (6). Thus, the contribution to aberration of the overall objective optical system is small. Furthermore, it is possible to reduce the size of the objective optical system.

Therefore, according to a preferable aspect of the present embodiment, it is desirable that the conditional expression (4) and the conditional expression (5) be satisfied and, at the same time, the following conditional expression (6) is satisfied:

$$0.6 < fG1/F < 2.2 \quad (6)$$

where
fG1 is the focal length of the first group G1, and
F is the focal length of the overall objective optical system at a time of focusing to the object point at the long distance.

The conditional expression (6) relates to an appropriate ratio of fG1 and F. Falling below the lower limit value of the conditional expression (6) is not preferable because if so, chromatic aberration of magnification of C line and F line is overcorrected.

Furthermore, exceeding the upper limit value of the conditional expression (6) is not preferable because if so, the balance of longitudinal chromatic aberration is lost. Furthermore, it is not preferable because chromatic aberration of magnification is undercorrected. Both cases lead to reduction in contrast involving color blurring on the periphery of a screen.

Furthermore, the conditional expression (6) also contributes to size reduction of the overall objective optical system. When the conditional expression (6) takes a value larger than the upper limit value thereof, the positive refractive power becomes small. Thus, it becomes difficult to reduce the overall length of the objective optical system. Moreover, since the height of light beam incident on the first lens L1 becomes high, the size of the optical system is also increased.

It is preferable that the following conditional expression (6') be satisfied instead of the conditional expression (6).

$$1.0 < fG1/F < 1.8 \quad (6')$$

Within a range of the lower limit of the conditional expression (6'), it is possible to correct curvature of field more favorably. Furthermore, within a range of the upper limit of the conditional expression (6'), it is possible to further reduce the size of the objective optical system.

Furthermore, according to a preferable aspect of the present embodiment, it is desirable that the following conditional expression (7) be satisfied:

$$-18 < fG2/F < -4.5 \quad (7)$$

where
fG2 is the focal length of the second group G2, and
F is the focal length of the overall objective optical system at a time of focusing to the object point at the long distance.

The conditional expression (7) relates to the focal length of the second group G2. The second group G2 distributes the refractive power together with the third group G3. The second group G2 serves the focusing function for matching the image plane according to change in object point distance.

When such a movable lens group is constructed, clearance between a movable frame and a fixed frame occurs because of the structure of frames holding the lenses. Therefore, when a movable frame exists, the amount of decentration of lenses becomes large, compared with a lens group only with a fixed frame.

If the refractive power of a lens group is large, it is necessary to minimize the amount of decentration at a time of driving of lenses even when the clearance between the frames is reduced. Therefore, it is desirable that the refractive power of the second group G2 that is a drive lens be within a range that satisfies the conditional expression (7).

When the conditional expression (7) takes a value smaller than the lower limit value thereof, the refractive power of the second group G2 becomes small, and it is possible to reduce error sensitivity due to decentration. However, it is not preferable because the moving distance of the second group G2 becomes large.

When the conditional expression (7) takes a value larger than the upper limit value thereof, the refractive power of the second group G2 becomes excessively large, and optical performance degradation is significant when the frames are decentered from each other.

Furthermore, according to a preferable aspect of the present embodiment, it is desirable that the following the conditional expression (8) be satisfied:

$$-10 < fG3/F < -3 \quad (8)$$

where
fG3 is the focal length of the third group G3, and
F is the focal length of the overall objective optical system at a time of focusing to the object point at the long distance.

The conditional expression (8) relates to the focal length of the third group G3. The third group G3 distributes the refractive power together with the second group G2. The third group G3 serves the focusing function for matching the image plane according to change in object point distance.

When such a movable lens group is constructed, a clearance occurs between a movable frame and a fixed frame because of the structure of frames holding the lenses. Therefore, when the optical system includes a movable frame, the amount of decentration of lenses becomes large, compared with a lens group only with a fixed frame.

If the refractive power of the lens group is large, it is necessary to minimize the amount of decentration at a time of driving of lenses even when the clearance between the frames is reduced. Therefore, it is desirable that the refractive power of the third group G3 that is a drive lens be within a range that satisfies the conditional expression (8).

When the conditional expression (8) takes a value smaller than the lower limit value thereof, the refractive power of the third group G3 becomes excessively large, and optical performance degradation becomes significant when the frames are decentered from each other. Furthermore, when the conditional expression (8) takes a value larger than the upper limit value thereof, the refractive power becomes small, and it is possible to reduce error sensitivity due to decentration. However, it is not preferable because the moving distance of the third group G3 becomes large.

Furthermore, according to a preferable aspect of the present embodiment, it is desirable that the following conditional expression (9) be satisfied:

$$1 < fG4/F < 5 \quad (9)$$

where fG4 is the focal length of the fourth group G4, and

F is the focal length of the overall objective optical system at a time of focusing to the object point at the long distance.

The conditional expression (9) contributes to correction of curvature of field. When the conditional expression (9) takes a value smaller than the lower limit value thereof, the image plane is inclined toward the under side. When the conditional expression (9) takes a value larger than the upper limit value thereof, the image plane is inclined toward the over side. Therefore, it is not preferable because an image is out of focus at the center area and the peripheral area of a screen.

It is preferable that the following conditional expression (9') be satisfied instead of the conditional expression (9).

$$2 < fG4/F < 4 \tag{9'}$$

Within a range that satisfies the conditional expression (9'), correction of curvature of field is more favorable.

Furthermore, according to a preferable aspect of the present embodiment, it is desirable that the following conditional expression (10) be satisfied:

$$1 < fG1S/F < 8 \tag{10}$$

where fG1S is a combined focal length from the first group G1 to the aperture stop S at a time of focusing to the object point at the long distance, and F is the focal length of the overall objective optical system at a time of focusing to the object point at the long distance.

The conditional expression (10) contributes to correction of chromatic aberration and correction of curvature of field. When the conditional expression (10) takes a value smaller than the lower limit value thereof, the image plane is inclined toward the over side. Furthermore, the aberration curve of F line of chromatic aberration of magnification is greatly inclined toward the over side.

When the conditional expression (10) takes a value larger than the upper limit value thereof, the image plane is inclined toward the under side. Then, the aberration curve of F line at a time of focusing to the object point at the long distance and the aberration curve of C line at a time of focusing to the object point at the close distance are inclined toward the over side, and therefore it is not preferable.

Moreover, the focal length in the front group with respect to the aperture stop S becomes larger. Therefore, the focus position in the front group with respect to the aperture stop S is positioned farther from the object. This is not preferable because the size of the overall objective optical system is increased. Moreover, the influence on the angle of view is significant, and it is difficult to achieve a wider angle. Therefore, it becomes impossible to maintain the observation angle of view necessary for observation by the endoscope.

It is preferable that the following conditional expression (10') be satisfied instead of the conditional expression (10). By limiting the upper limit value of the conditional expression (10), it becomes possible to contribute to further size reduction.

$$1 < fG1S/F < 5.5 \tag{10'}$$

Within a range that satisfies the conditional expression (10'), correction of curvature of field is more favorable.

Furthermore, according to a preferable aspect of the present embodiment, it is desirable that the following conditional expression (11) be satisfied:

$$2 < fGS4/F < 7 \tag{11}$$

where fGS4 is a combined focal length from the aperture stop S to the fourth group G4 at a time of focusing to the object point at the long distance, and F is the focal length of the overall objective optical system at a time of focusing to the object point at the long distance.

The conditional expression (11) contributes to correction of chromatic aberration and correction of curvature of field. When the conditional expression (11) takes a value smaller than the lower limit value thereof, the image plane is inclined toward the under side. Moreover, the aberration curve of F line of longitudinal chromatic aberration of magnification is greatly inclined toward the over side.

When the conditional expression (11) takes a value larger than the upper limit value thereof, the image plane is inclined toward the over side. In particular, chromatic aberration of magnification at a time of focusing to the object point at the long distance is degraded. The aberration curve of F line is greatly inclined toward the under side. The aberration curve of C line is greatly inclined toward the over side. In this case, degradation of a peripheral image is significant and this is not preferable.

It is preferable that the following conditional expression (11') be satisfied instead of the conditional expression (11). When the conditional expression (11) is limited as described below, correction of curvature of field and chromatic aberration of magnification is more favorable.

$$2.4 < fGS4/F < 6.2 \tag{11'}$$

Furthermore, according to a preferable aspect of the present embodiment, it is desirable that the following the conditional expression (12) be satisfied:

$$0.5 < fG2/fG3 < 3.5 \tag{12}$$

where fG2 is the focal length of the second group G2, and fG3 is the focal length of the third group G3.

The conditional expression (12) relates to a ratio for making the refractive powers of the second group G2 and the third group G3 appropriate. In this case, it is possible to suppress image plane variation at a time of focusing. Furthermore, it is possible to contribute to size reduction of the objective optical system.

When the conditional expression (12) takes a value smaller than the lower limit value thereof, the refractive power of the second group G2 becomes excessively large. Then, variation in curvature of field involved with focusing becomes large. Accordingly, a significant difference occurs between an image plane position at a time of normal observation (at a time of focusing to the object point at the long distance) and an image plane position at a time of focusing to the object point at the close distance. Furthermore, since the refractive power of the third group G3 becomes small, the moving distance of the third group G3 increases. Therefore, it is not preferable because the size of the overall objective optical system is increased.

Furthermore, when the conditional expression (12) takes a value larger than the upper limit value thereof, the refractive power of the third group G3 becomes excessively large. In this case, chromatic aberration of magnification becomes large. Furthermore, variation in image plane at a time of focusing also increases, and therefore this is not preferable.

Furthermore, according to a preferable aspect of the present embodiment, it is desirable that the following conditional expression (13) be satisfied:

$$1.5 < fG4/fG1 < 3.5 \quad (13)$$

where fG4 is the focal length of the fourth group G4, and
fG1 is the focal length of the first group G1.

The conditional expression (13) relates to a ratio for making the refractive powers of the first group G1 and the fourth group G4 appropriate. It is a conditional expression that contributes to size reduction of the overall objective optical system.

When the conditional expression (13) takes a value smaller than the lower limit value thereof, the refractive power of the first group G1 becomes excessively small. Then, the height of light beam incident on the first lens L1 increases. Therefore, the lens diameter of the lens in the first group G1 becomes large.

When the conditional expression (13) takes a value larger than the upper limit value thereof, the refractive power of the first group G1 becomes excessively small. Therefore, the focus position by the first group G1 is shifted toward the image plane side. Consequently, the overall length increases, and the size of the entire lens system is increased.

It is preferable that the following conditional expression (13') be satisfied instead of the conditional expression (13). The upper limit of the conditional expression (13) may be limited as described below.

$$1.5 < fG4/fG1 < 3 \quad (13')$$

Accordingly, within a range of the upper limit of the conditional expression (13'), further size reduction is possible.

Furthermore, according to a preferable aspect of the present embodiment, it is desirable that the following the conditional expression (14) be satisfied:

$$-4 < fG3/fG4 < -1 \quad (14)$$

where fG3 is the focal length of the third group G3, and
fG4 is the focal length of the fourth group G4.

The conditional expression (14) relates to aberration correction at a time of focusing to the object point at the long distance. An aberration that occurs in the first lens L1 having a negative refractive power in the first group G1 is corrected by the third group G3 and the fourth group G4 that are rear-side lens groups.

Therefore, it is necessary to make the refractive powers of the third group G3 and the fourth group G4 appropriate. Falling below the lower limit value of the conditional expression (14) is not preferable because if so, in particular, longitudinal chromatic aberration becomes large. Exceeding the upper limit value of the conditional expression (14) is not preferable because if so, chromatic aberration of magnification becomes large.

Furthermore, according to a preferable aspect of the present embodiment, it is desirable that the following the conditional expression (15) be satisfied:

$$2.5 < Fno < 5.2 \quad (15)$$

where

Fno is the F value of the objective optical system at a time of focusing to the object point at the long distance.

The conditional expression (15) relates to Fno of the objective optical system. When the conditional expression (15) takes a value smaller than the lower limit value thereof, it is possible to implement a bright optical system. However, it is not preferable because the depth of field becomes shallow.

When the conditional expression (15) takes a value larger than the upper limit value thereof, it is impossible to obtain optical performance in spatial frequencies corresponding to high-definition image sensors due to the effect of diffraction limit.

Furthermore, according to a preferable aspect of the present embodiment, it is desirable that the following conditional expression (16) be satisfied:

$$0.8 < Fno/Fno\_N < 1.2 \quad (16)$$

where

Fno is the F value of the objective optical system at a time of focusing to the object point at the long distance, and
Fno_N is the F value of the objective optical system at a time of focusing to the object point at the close distance.

The conditional expression (16) relates to a ratio of Fno at a time of focusing to the object point at the long distance and Fno at a time of focusing to the object point at the close distance. The difference between Fno at a time of focusing to the object point at the long distance and Fno at a time of focusing to the object point at the close distance is preferably smaller, desirably in a range of the conditional expression.

Based on Fno, the diameter of a least circle of confusion at the image plane is determined by the following Expression (A).

$$\text{(Diameter of least circle of confusion at image plane)} = 1.22 \times (Fno) \times (\text{wavelength}) \quad (A)$$

According to Expression (A) above, when Fno is large, the diameter of a least circle of confusion is large. Then, it becomes impossible to be support an image sensor with high resolution, and image quality is degraded. Therefore, it is preferable that the difference between Fno at a time of focusing to the object point at the close distance and Fno at a time of focusing to the object point at the long distance be not larger. It is not preferable that the difference in Fno exceed the range of the conditional expression (16) because if so, the difference in image quality at a time of focusing becomes large.

Falling below the lower limit value of the conditional expression (16) is not preferable because if so, image quality degradation at a time of focusing to the object point at the close distance becomes large. Furthermore, exceeding the upper limit value of the conditional expression (16) is not preferable because if so, image quality degradation at a time of focusing to the object point at the long distance becomes large.

Example 1

An objective optical system according to Example 1 will be explained.

Figure 2B:
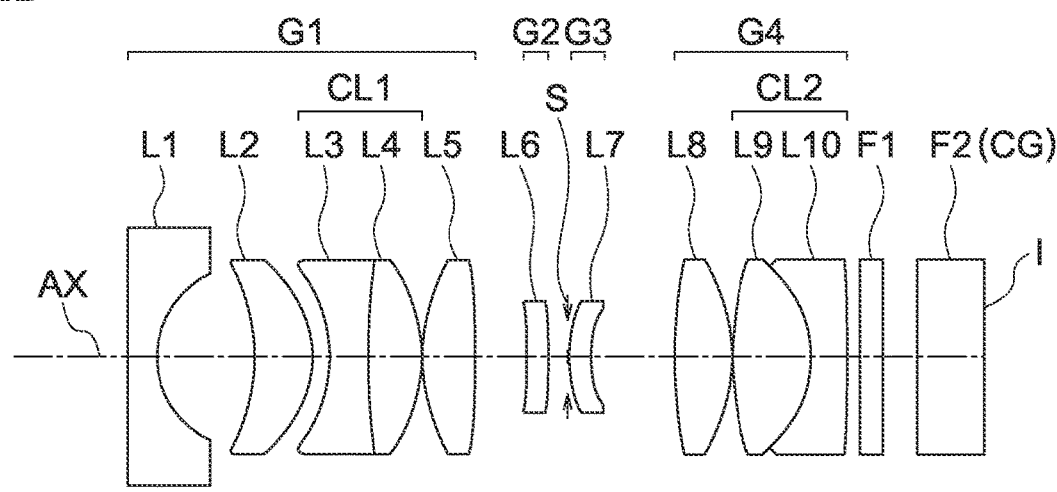

FIG. 2A is a sectional view in a normal observation state (at a time of focusing to the object point at the long distance) of the objective optical system according to the present example, and FIG. 2B is a sectional view in a close observation state (at a time of focusing to the object point at the close distance).

As illustrated in FIG. 2A and FIG. 2B, the objective optical system includes, in order from the object side: a positive first group G1; a negative second group G2; an aperture stop S; a negative third group G3; and a positive fourth group G4.

The positive first group G1 includes, in order from the object side: a plano-concave negative first lens L1 having a flat surface directed toward the object; a positive second meniscus lens L2 having a convex surface directed toward the image side; a biconcave negative third lens L3; a biconvex positive fourth lens L4; and a biconvex positive fifth lens L5. The negative third lens L3 and the positive fourth lens L4 form a cemented lens CL1.

The negative second group G2 includes a negative sixth meniscus lens L6 having a convex surface directed toward the image side. The negative sixth meniscus lens L6 moves along an optical axis AX toward the image side (image plane I) at a time of focusing from the normal observation state (FIG. 2A) to the close observation state (FIG. 2B).

The negative third group G3 includes a negative seventh meniscus lens L7 having a convex surface directed toward the object. The negative seventh meniscus lens L7 moves along the optical axis AX toward the image side (image plane I) at a time of focusing from the normal observation state (FIG. 2A) to the close observation state (FIG. 2B).

The aperture stop S is disposed on the front side (object side) of the third group G3.

The positive fourth group G4 includes, in order from the object side: a biconvex positive eighth lens L8; a biconvex positive ninth lens L9; and a negative tenth meniscus lens L10 having a convex surface directed toward the image side. The positive ninth lens L9 and the negative tenth meniscus lens L10 form a cemented lens CL2.

On the back (image plane I side) of the fourth group G4, a parallel plate F1 and a parallel plate F2 are disposed in order from the object side. The parallel plate F2 is fixed as a cover glass CG to a front surface of a not-illustrated image sensor.

The parallel plate F1 is a filter for cutting off specific wavelengths, for example, 1060 nm of YAG laser, 810 nm of semiconductor laser, or the infrared band.

FIG. 3A, FIG. 3B, FIG. 3C, and FIG. 3D illustrate spherical aberration (SA), astigmatism (AS), distortion (DT), and chromatic aberration of magnification (CC) in the normal observation state in this example. FIG. 3E, FIG. 3F, FIG. 3G, and FIG. 3H illustrate spherical aberration (SA), astigmatism (AS), distortion (DT), and chromatic aberration of magnification (CC) in the close observation state in this example.

These aberration diagrams illustrate the wavelengths of 656.3 nm (C line), 486.1 nm (F line), and 546.1 nm (e line). Furthermore, in the drawings, "co" denotes a half angle of view. Hereinafter, similar reference signs are used for aberration diagrams.

Example 2

Figure 4A:
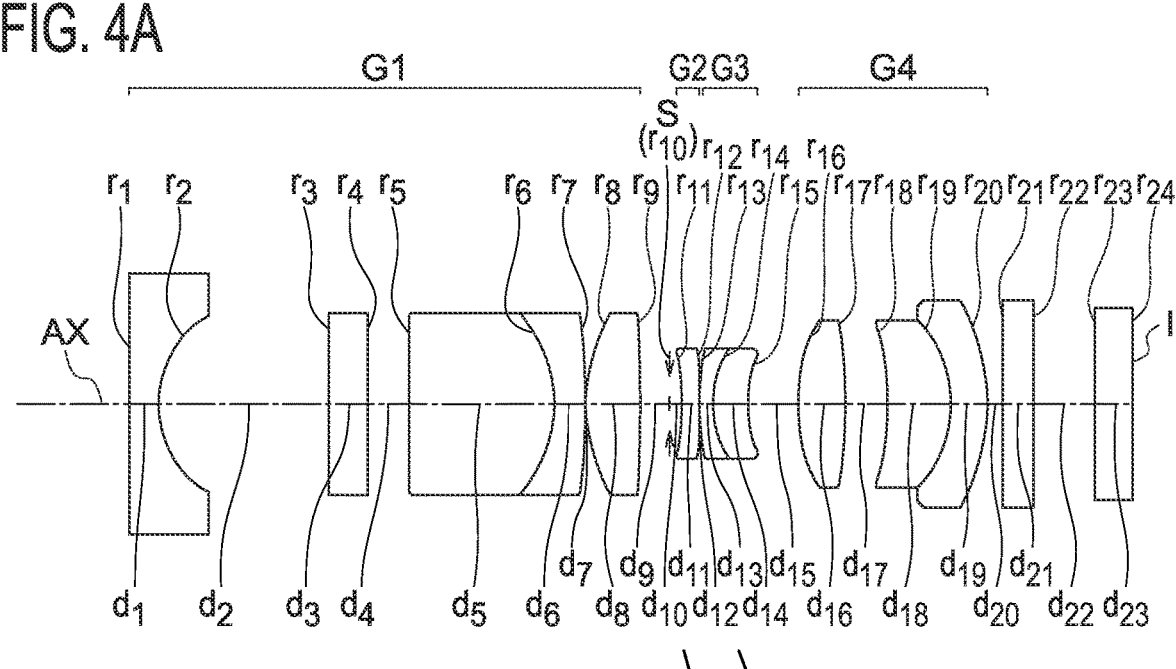

An objective optical system according to Example 2 will be explained. FIG. 4A is a sectional view in a normal observation state (the object point at the long distance) of the objective optical system according to the present example, and FIG. 4B is a sectional view in a close observation state (the object point at the close distance).

Figure 4B:
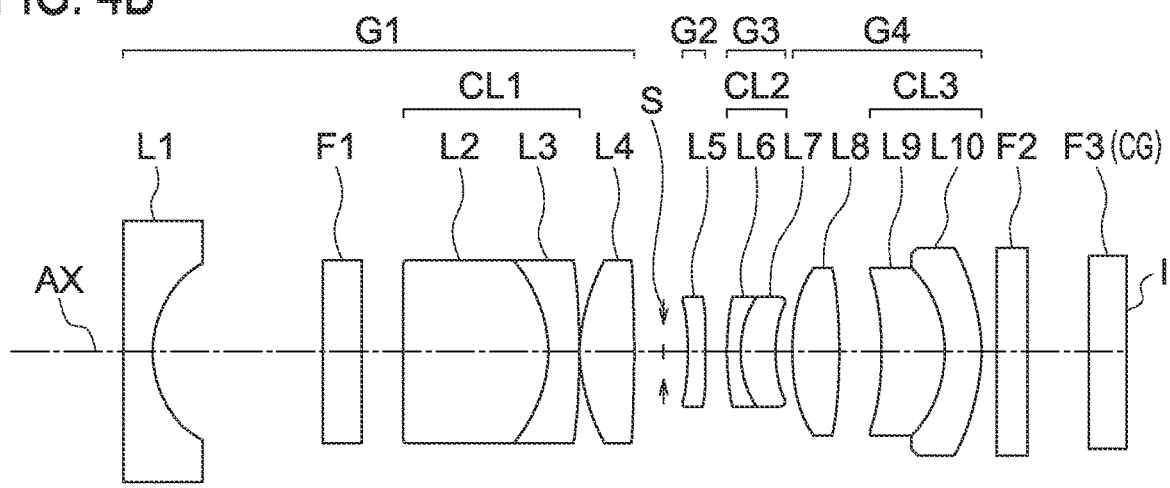

As illustrated in FIG. 4A and FIG. 4B, the objective optical system includes, in order from the object side: a positive first group G1; an aperture stop S; a negative second group G2; a negative third group G3; and a positive fourth group G4.

The positive first group G1 includes, in order from the object side: a plano-concave negative first lens L1 having a flat surface directed toward the object; a parallel plate F1; a positive second meniscus lens L2 having a convex surface directed toward the image side; a negative third meniscus lens L3 having a convex surface directed toward the image side; and a biconvex positive fourth lens L4. The positive second meniscus lens L2 and the negative third meniscus lens L3 form a cemented lens CL1.

The aperture stop S is disposed on the rear side (image plane I side) of the first group G1.

The negative second group G2 includes a negative fifth meniscus lens L5 having a convex surface directed toward the image side. The negative fifth meniscus lens L5 moves along an optical axis AX toward the image side (image plane I) at a time of focusing from the normal observation state (FIG. 4A) to the close observation state (FIG. 4B).

The negative third group G3 includes a negative sixth meniscus lens L6 having a convex surface directed toward the object and a positive seventh meniscus lens L7 having a convex surface directed toward the object. The negative sixth meniscus lens L6 and the positive seventh meniscus lens L7 form a cemented lens CL2. The cemented lens CL2 moves along the optical axis AX toward the image side (image plane I) at a time of focusing from the normal observation state (FIG. 4A) to the close observation state (FIG. 4B).

The positive fourth group G4 includes, in order from the object side: a biconvex positive eighth lens L8; a positive ninth meniscus lens L9 having a convex surface directed toward the image side; and a negative tenth meniscus lens L10 having a convex surface directed toward the image side. The positive ninth meniscus lens L9 and the negative tenth meniscus lens L10 form a cemented lens CL3.

On the rear side (image plane I side) of the fourth group G4, a parallel plate F2 and a parallel plate F3 are disposed. The parallel plate F3 is fixed as a cover glass CG to a front surface of a not-illustrated image sensor.

The parallel plate F1 and the parallel plate F2 are filters for cutting off specific wavelengths, for example, 1060 nm of YAG laser, 810 nm of semiconductor laser, or the infrared band.

FIG. 5A, FIG. 5B, FIG. 5C, and FIG. 5D illustrate spherical aberration (SA), astigmatism (AS), distortion (DT), and chromatic aberration of magnification (CC) in the normal observation state in this example. FIG. 5E, FIG. 5F, FIG. 5G, and FIG. 5H illustrate spherical aberration (SA), astigmatism (AS), distortion (DT), and chromatic aberration of magnification (CC) in the close observation state in this example.

Example 3

Figure 6A:
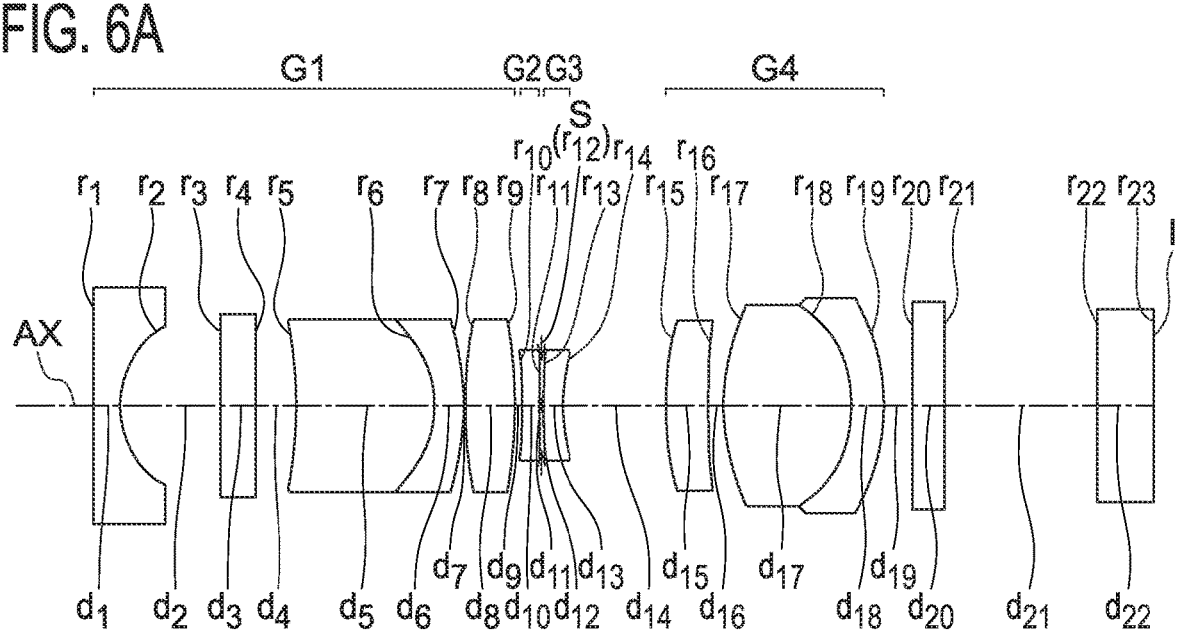

An objective optical system according to Example 3 will be explained. FIG. 6A is a sectional view in a normal observation state (the object point at the long distance) of the objective optical system according to the present example, and FIG. 6B is a sectional view in a close observation state (the object point at the close distance).

Figure 6B:
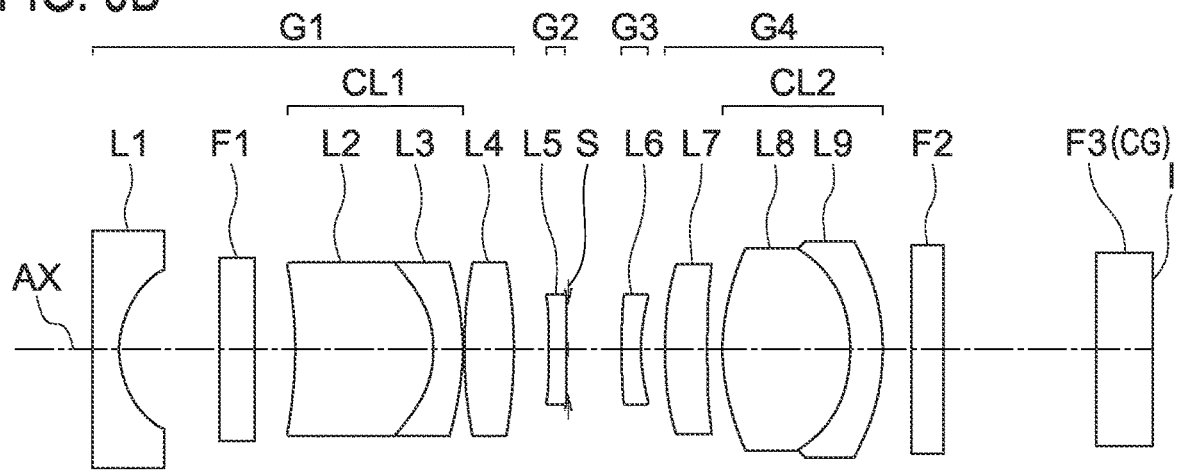

As illustrated in FIG. 6A and FIG. 6B, the objective optical system includes, in order from the object side: a positive first group G1; a negative second group G2; an aperture stop S; a negative third group G3; and a positive fourth group G4.

The positive first group G1 includes, in order from the object side: a plano-concave negative first lens L1 having a flat surface directed toward the object; a parallel plate F1; a positive second meniscus lens L2 having a convex surface directed toward the image side; a negative third meniscus lens L3 having a convex surface directed toward the image side; and a biconvex positive fourth lens L4. The positive second meniscus lens L2 and the negative third meniscus lens L3 form a cemented lens CL1.

The negative second group G2 includes a negative fifth meniscus lens L5 having a convex surface directed toward the image side. The negative fifth meniscus lens L5 moves along an optical axis AX toward the image side (image plane I) at a time of focusing from the normal observation state (FIG. 6A) to the close observation state (FIG. 6B).

The aperture stop S is disposed on the rear side (image plane I side) of the second group G2.

The negative third group G3 includes a negative sixth meniscus lens L6 having a convex surface directed toward the object. The negative sixth lens L6 moves along the optical axis AX toward the image side (image plane I) at a time of focusing from the normal observation state (FIG. 6A) to the close observation state (FIG. 6B).

The positive fourth group G4 includes, in order from the object side: a positive seventh meniscus lens L7 having a convex surface directed toward the object; a biconvex positive eighth lens L8; and a negative ninth meniscus lens L9 having a convex surface directed toward the image side. The positive eighth lens L8 and the negative ninth meniscus lens L9 form a cemented lens CL2.

On the rear side (image plane I side) of the fourth group G4, a parallel plate F2 and a parallel plate F3 are disposed. The parallel plate F3 is fixed as a cover glass CG to a front surface of a not-illustrated image sensor.

The parallel plate F1 and the parallel plate F2 are filters for cutting off specific wavelengths, for example, 1060 nm of YAG laser, 810 nm of semiconductor laser, or the infrared band.

FIG. 7A, FIG. 7B, FIG. 7C, and FIG. 7D illustrate spherical aberration (SA), astigmatism (AS), distortion (DT), and chromatic aberration of magnification (CC) in the normal observation state in this example. FIG. 7E, FIG. 7F, FIG. 7G, and FIG. 7H illustrate spherical aberration (SA), astigmatism (AS), distortion (DT), and chromatic aberration of magnification (CC) in the close observation state in this example.

Example 4

Figure 8A:
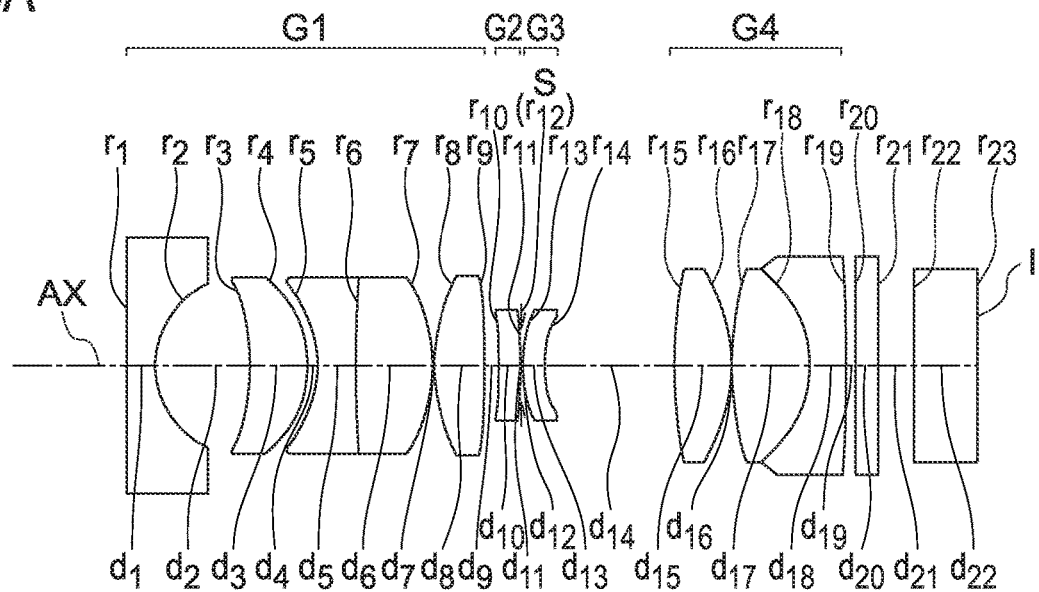

An objective optical system according to Example 4 will be explained. FIG. 8A is a sectional view in a normal observation state (the object point at the long distance) of the objective optical system according to the present example, and FIG. 8B is a sectional view in a close observation state (the object point at the close distance).

Figure 8B:
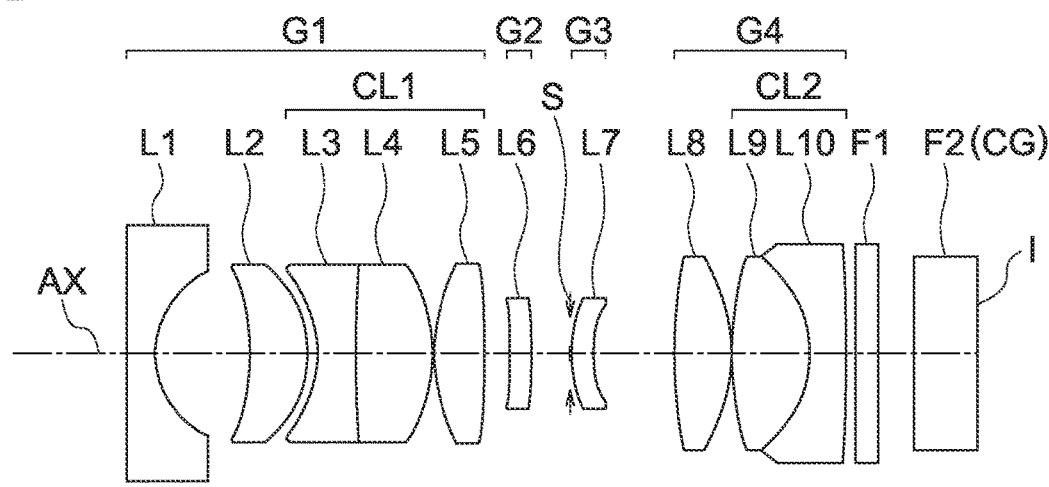

As illustrated in FIG. 8A and FIG. 8B, the objective optical system includes, in order from the object side: a positive first group G1; a negative second group G2; an aperture stop S: a negative third group G3; and a positive fourth group G4.

The positive first group G1 includes, in order from the object side: a plano-concave negative first lens L1 having a flat surface directed toward the object; a positive second meniscus lens L2 having a convex surface directed toward the image side; a biconcave negative third lens L3; a biconvex positive fourth lens L4; and a biconvex positive fifth lens L5. The negative third lens L3 and the positive fourth lens L4 form a cemented lens CL1.

The negative second group G2 includes a negative sixth meniscus lens L6 having a convex surface directed toward the image side. The negative sixth meniscus lens L6 moves along an optical axis AX toward the image side (image plane I) at a time of focusing from the normal observation state (FIG. 8A) to the close observation state (FIG. 8B).

The negative third group G3 includes a negative seventh meniscus lens L7 having a convex surface directed toward the object. The negative seventh meniscus lens L7 moves along the optical axis AX toward the image side (image plane I) at a time of focusing from the normal observation state (FIG. 8A) to the close observation state (FIG. 8B).

The aperture stop S is disposed on the front side (object side) of the third group G3.

The positive fourth group G4 includes, in order from the object side: a biconvex positive eighth lens L8; a biconvex positive ninth lens L9; and a negative tenth meniscus lens L10 having a convex surface directed toward the image side. The positive ninth lens L9 and the negative tenth meniscus lens L10 form a cemented CL2.

On the rear side (image plane I side) of the fourth group G4, a parallel flat F1 and a parallel plate F2 are disposed. The parallel plate F2 is fixed as a cover glass CG to a front surface of a not-illustrated image sensor.

The parallel plate F1 is a filter for cutting off specific wavelengths, for example, 1060 nm of YAG laser, 810 nm of semiconductor laser, or the infrared band.

FIG. 9A, FIG. 9B, FIG. 9C, and FIG. 9D illustrate spherical aberration (SA), astigmatism (AS), distortion (DT), and chromatic aberration of magnification (CC) in the normal observation state in this example. FIG. 9E, FIG. 9F, FIG. 9G, and FIG. 9H illustrate spherical aberration (SA), astigmatism (AS), distortion (DT), and chromatic aberration of magnification (CC) in the close observation state in this example.

Example 5

Figure 10A:
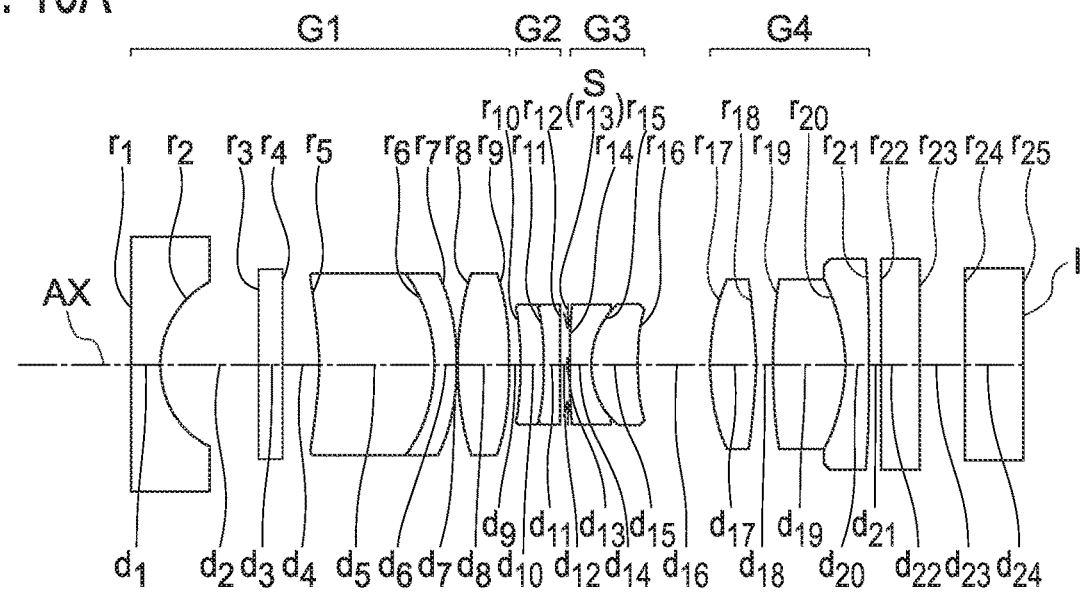

An objective optical system according to Example 5 will be explained. FIG. 10A is a sectional view in a normal observation state (the object point at the long distance) of the objective optical system according to the present example, and FIG. 10B is a sectional view in a close observation state (the object point at the close distance).

Figure 10B:
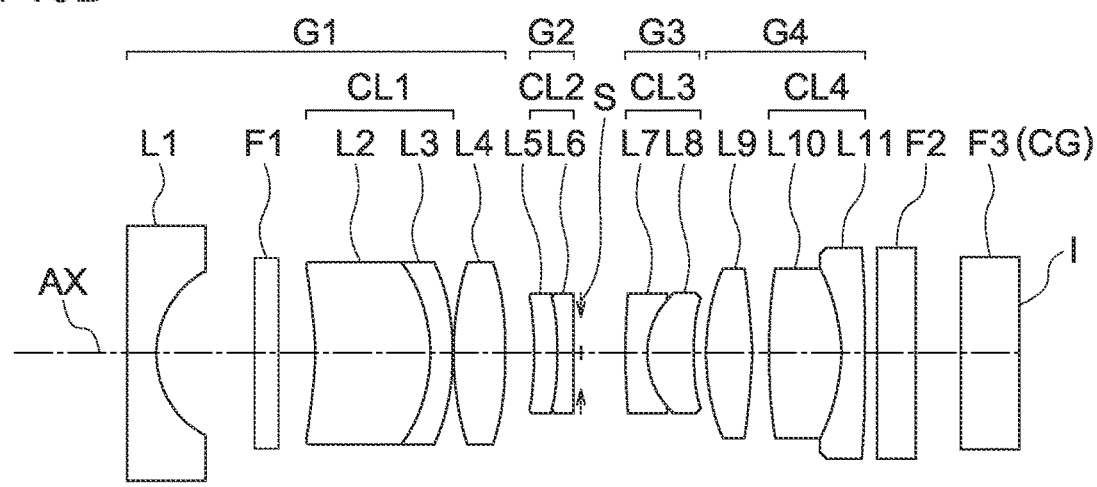

As illustrated in FIG. 10A and FIG. 10B, the objective optical system includes, in order from the object side: a positive first group G1; a negative second group G2; an aperture stop S; a negative third group G3; and a positive fourth group G4.

The positive first group G1 includes, in order from the object side: a plano-concave negative first lens L1 having a flat surface directed toward the object; a parallel plate F1; a positive second meniscus lens L2 having a convex surface directed toward the image side; a negative third meniscus lens L3 having a convex surface directed toward the image side; and a biconvex positive fourth lens L4. The positive second meniscus lens L2 and the negative third meniscus lens L3 form a cemented lens CL1.

The negative second group G2 includes, in order from the object side: a positive fifth meniscus lens L5 having a convex surface directed toward the image side; and a negative sixth meniscus lens L6 having a convex surface directed toward the image side. The positive fifth meniscus lens L5 and the negative sixth meniscus lens L6 are cemented to form a cemented lens CL2. The cemented lens CL2 moves along an optical axis AX toward the image side (image plane I side) at a time of focusing from the normal observation state (FIG. 10A) to the close observation state (FIG. 10B).

The aperture stop S is disposed on the rear side (image plane I side) of the second group G2.

The negative third group G3 includes, in order from the object side: a negative seventh meniscus lens L7 having a convex surface directed toward the object; and a positive eighth meniscus lens L8 having a convex surface directed toward the object. The negative seventh meniscus lens L7 and the positive eighth meniscus lens L8 are cemented to forma CL3. The cemented lens CL3 moves along the optical axis AX toward the image side (image plane I side) at a time of focusing from the normal observation state (FIG. 10A) to the close observation state (FIG. 10B).

The positive fourth group G4 includes, in order from the object side: a biconvex positive ninth lens L9; a biconvex positive tenth lens L10; and a negative eleventh meniscus lens L11 having a convex surface directed toward the image side. The positive tenth lens L10 and the negative eleventh meniscus lens L11 form a cemented lens CL4.

On the rear side (image plane I side) of the fourth group G4, a parallel plate F2 and a parallel plate F3 are disposed. The parallel plate F3 is fixed as a cover glass CG to a front surface of a not-illustrated image sensor.

The parallel plate F1 and the parallel plate F2 are filters for cutting off specific wavelengths, for example, 1060 nm of YAG laser, 810 nm of semiconductor laser, or the infrared band.

FIG. 11A, FIG. 11B, FIG. 11C, and FIG. 11D illustrate spherical aberration (SA), astigmatism (AS), distortion (DT), and chromatic aberration of magnification (CC) in the normal observation state in this example. FIG. 11E, FIG. 11F, FIG. 11G, and FIG. 11H illustrate spherical aberration (SA), astigmatism (AS), distortion (DT), and chromatic aberration of magnification (CC) in the close observation state in this example.

Example 6

Figure 12A:
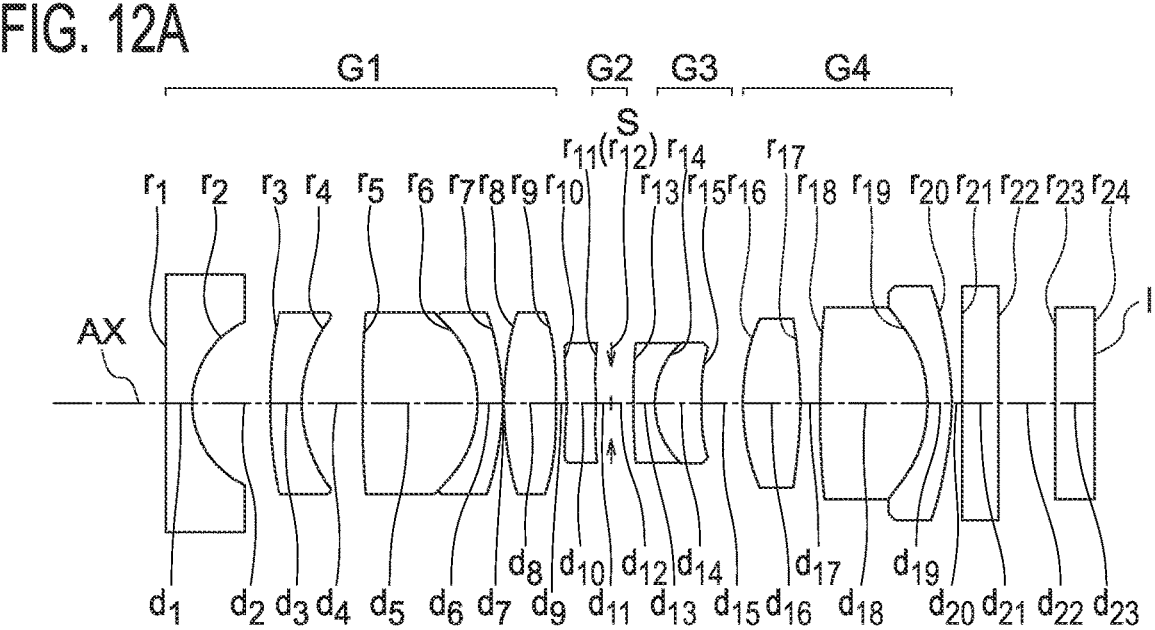

An objective optical system according to Example 6 will be explained. FIG. 12A is a sectional view in a normal observation state (the object point at the long distance) of the objective optical system according to the present example, and FIG. 12B is a sectional view in a close observation state (the object point at the close distance).

Figure 12B:
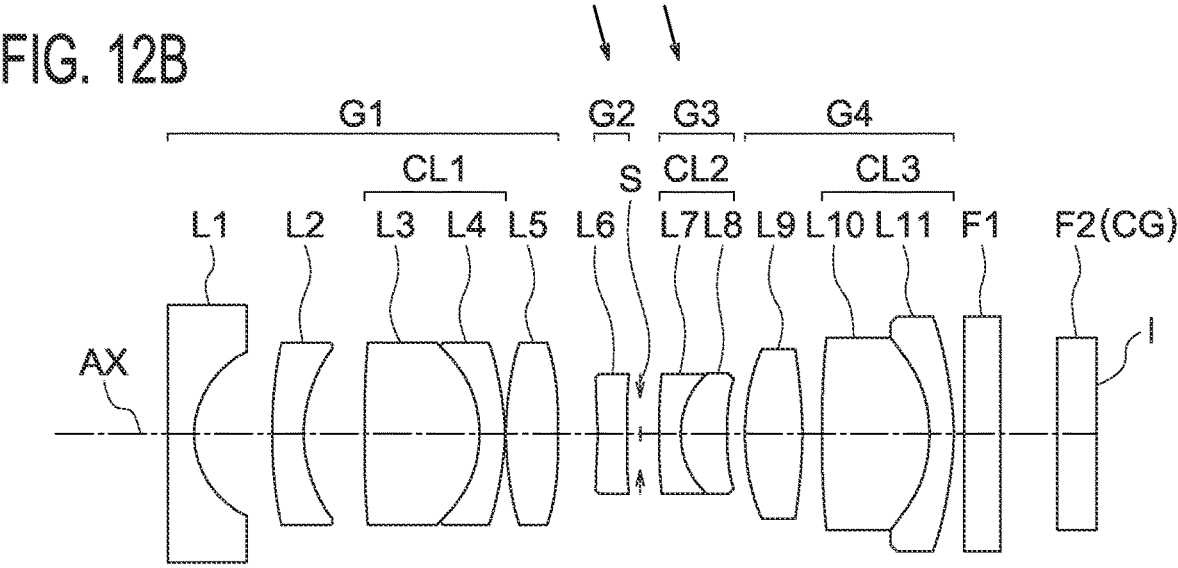

As illustrated in FIG. 12A and FIG. 12B, the objective optical system includes, in order from the object side: a positive first group G1; a negative second group G2; an aperture stop S; a negative third group G3; and a positive fourth group G4.

The positive first group G1 includes, in order from the object side: a plano-concave negative first lens L1 having a flat surface directed toward the object; a negative second meniscus lens L2 having a convex surface directed toward the object; a biconvex positive third lens L3; a negative fourth meniscus lens L4 having a convex surface directed toward the image side; and a biconvex positive fifth lens L5. The positive third lens L3 and the negative fourth meniscus lens L4 form a cemented lens CL1.

The negative second group G2 includes a biconcave negative sixth lens L6. The negative sixth lens L6 moves along an optical axis AX toward the image side (image plane I) at a time of focusing from the normal observation state (FIG. 12A) to the close observation state (FIG. 12B).

The aperture stop S is disposed on the rear side (image plane I side) of the second group G2.

The negative third group G3 includes, in order from the object side: a negative seventh meniscus lens L7 having a convex surface directed toward the object; and a positive eighth meniscus lens L8 having a convex surface directed toward the object. The negative seventh meniscus lens L7 and the positive eighth meniscus lens L8 form a cemented lens CL2. The cemented lens CL2 moves along the optical axis AX toward the image side (image plane I) at a time of focusing from the normal observation state (FIG. 12A) to the close observation state (FIG. 12B).

The positive fourth group G4 includes a biconvex positive ninth lens L9, a biconvex positive tenth lens L10, and a negative eleventh meniscus lens L11 having a convex surface directed toward the image side. The positive tenth lens L10 and the negative eleventh meniscus lens L11 form a cemented lens CL3.

On the rear side (image plane I side) of the fourth group G4, a parallel plate F1 and a parallel plate F2 are disposed. The parallel plate F2 is fixed as a cover glass CG to a front surface of a not-illustrated image sensor.

The parallel plate F1 is a filter for cutting off specific wavelengths, for example, 1060 nm of YAG laser, 810 nm of semiconductor laser, or the infrared band.

FIG. 13A, FIG. 13B, FIG. 13C, and FIG. 13D illustrate spherical aberration (SA), astigmatism (AS), distortion (DT), and chromatic aberration of magnification (CC) in the normal observation state in this example. FIG. 13E, FIG. 13F, FIG. 13G, and FIG. 13H illustrate spherical aberration (SA), astigmatism (AS), distortion (DT), and chromatic aberration of magnification (CC) in the close observation state in this example.

Example 7

An objective optical system according to Example 7 will be explained. FIG. 14A is a sectional view in a normal observation state (the object point at the long distance) of the objective optical system according to the present example, and FIG. 14B is a sectional view in a close observation state (the object point at the close distance).

As illustrated in FIG. 14A and FIG. 14B, the objective optical system includes, in order from the object side: a positive first group G1; a negative second group G2; an aperture stop S; a negative third group G3; and a positive fourth group G4.

The positive first group G1 includes, in order from the object side: a plano-concave negative first lens L1 having a flat surface directed toward the object; a parallel plate F1; a positive second meniscus lens L2 having a convex surface directed toward the image side; a negative third meniscus lens L3 having a convex surface directed toward the image side; and a biconvex positive fourth lens L4. The positive second meniscus lens L2 and the negative third meniscus lens L3 form a cemented lens CL1.

The negative second group G2 includes a biconcave fifth lens L5. The negative fifth lens L5 moves along an optical axis AX toward the image side (image plane I side) at a time of focusing from the normal observation state (FIG. 14A) to the close observation state (FIG. 14B).

The aperture stop S is disposed on the rear side (image plane I side) of the second group G2.

The negative third group G3 includes, in order from the object side: a negative sixth meniscus lens L6 having a convex surface directed toward the object; and a positive seventh meniscus lens L7 having a convex surface directed toward the object. The negative sixth meniscus lens L6 and the positive seventh meniscus lens L7 forma cemented lens CL2. The cemented lens CL2 moves along the optical axis AX toward the image side (image plane I side) at a time of focusing from the normal observation state (FIG. 14A) to the close observation state (FIG. 14B).

The positive fourth group G4 includes, in order from the object side: a biconvex positive eighth lens L8; a biconvex positive ninth lens L9; and a negative tenth meniscus lens L10 having a convex surface directed toward the image side. The positive ninth lens L9 and the negative tenth meniscus lens L10 form a cemented CL3.

On the rear side (image plane I side) of the fourth group G4, a parallel plate F2 and a parallel plate F3 are disposed. The parallel plate F3 is fixed as a cover glass CG to a front surface of a not-illustrated image sensor.

The parallel plate F1 and the parallel plate F2 are filters for cutting off specific wavelengths, for example, 1060 nm of YAG laser, 810 nm of semiconductor laser, or the infrared band.

FIG. 15A, FIG. 15B, FIG. 15C, and FIG. 15D illustrate spherical aberration (SA), astigmatism (AS), distortion (DT), and chromatic aberration of magnification (CC) in the normal observation state in this example. FIG. 15E, FIG. 15F, FIG. 15G, and FIG. 15H illustrate spherical aberration (SA), astigmatism (AS), distortion (DT), and chromatic aberration of magnification (CC) in the close observation state in this example.

Example 8

Figure 16A:
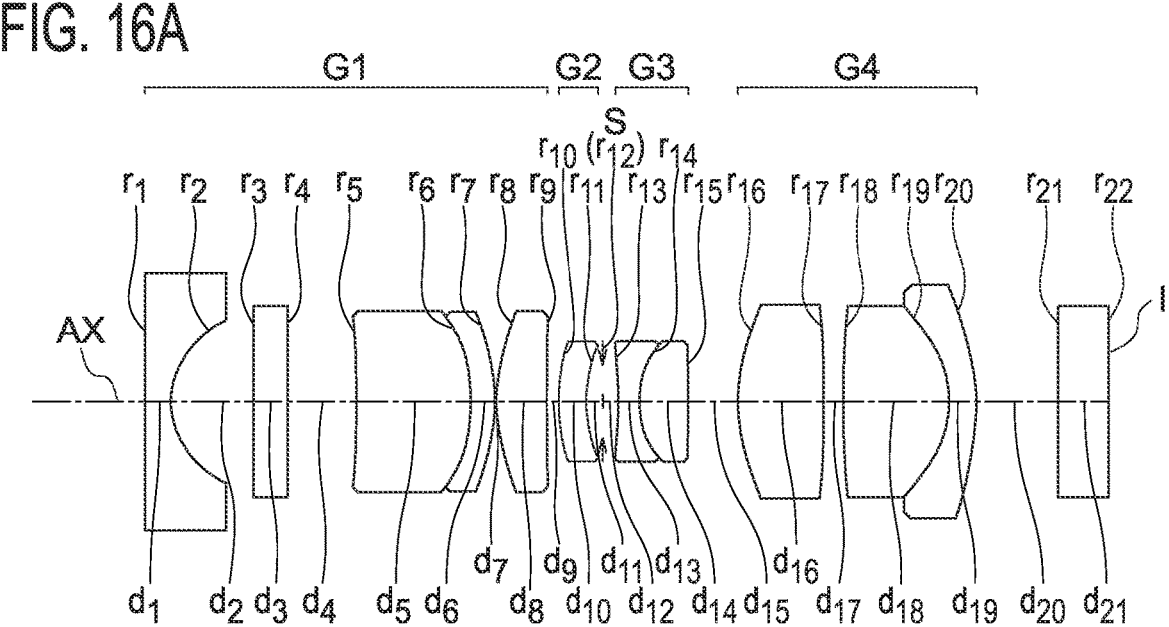

An objective optical system according to Example 8 will be explained. FIG. 16A is a sectional view in a normal observation state (the object point at the long distance) of the objective optical system according to the present example, and FIG. 16B is a sectional view in a close observation state (the object point at the close distance).

Figure 16B:
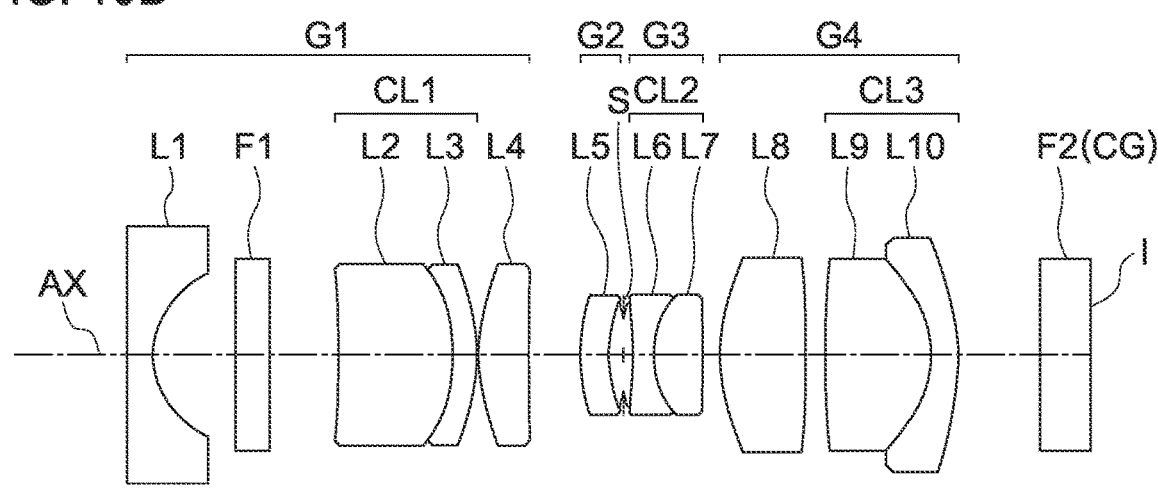

As illustrated in FIG. 16A and FIG. 16B, the objective optical system includes, in order from the object side: a positive first group G1; a negative second group G2, an aperture stop S; a negative third group G3; and a positive fourth group G4.

The positive first group G1 includes, in order from the object side: a plano-concave negative first lens L1 having a flat surface directed toward the object; a parallel plate F1; a positive second meniscus lens L2 having a convex surface directed toward the image side; a negative third meniscus lens L3 having a convex surface directed toward the image side; and a positive fourth meniscus lens L4 having a convex surface directed toward the object. The positive second meniscus lens L2 and the negative third meniscus lens L3 form a cemented lens CL1.

The negative second group G2 includes a negative fifth meniscus lens L5 having a convex surface directed toward the object. The negative fifth meniscus lens L5 moves along an optical axis AX toward the image side (image plane I side) at a time of focusing from the normal observation state (FIG. 16A) to the close observation state (FIG. 16B).

The aperture stop S is disposed on the rear side (image plane I side) of the second group G2.

The negative third group G3 includes, in order from the object side: a biconcave negative sixth lens L6; and a biconvex positive seventh lens L7. The negative sixth lens L6 and the positive seventh lens L7 forma cemented lens CL2. The cemented lens CL2 moves along the optical axis AX toward the image side (image plane I side) at a time of focusing from the normal observation state (FIG. 16A) to the close observation state (FIG. 16B).

The positive fourth group G4 includes, in order from the object side: a biconvex positive eighth lens L8; a biconvex positive ninth lens L9; and a negative tenth meniscus lens L10 having a convex surface directed toward the image side. The positive ninth lens L9 and the negative tenth meniscus lens L10 form a cemented CL3.

On the rear side (image plane I side) of the fourth group G4, a parallel plate F2 is disposed.

The parallel plate F2 is fixed as a cover glass CG to a front surface of a not-illustrated image sensor.

The parallel plate F1 is a filter for cutting off specific wavelengths, for example, 1060 nm of YAG laser, 810 nm of semiconductor laser, or the infrared band.

FIG. 17A, FIG. 17B, FIG. 17C, and FIG. 17D illustrate spherical aberration (SA), astigmatism (AS), distortion (DT), and chromatic aberration of magnification (CC) in the normal observation state in this example. FIG. 17E, FIG. 17F, FIG. 17G, and FIG. 17H illustrate spherical aberration (SA), astigmatism (AS), distortion (DT), and chromatic aberration of magnification (CC) in the close observation state in this example.

Numerical data of the examples described above is shown below. The symbol r represents a radius of curvature of each lens surface, d represents the distance between lens surfaces, ne represents the refractive index for e line of each lens, vd represents the Abbe number of each lens, Fno represents F number, 2ω represents a full angle of view, and IH represents an image height. Stop denotes an aperture stop.

Example 1

| Unit mm | | | | |
|---|---|---|---|---|
| Surface data | | | | |
| Surface no. | r | d | ne | vd |
| 1 | ∞ | 0.380 | 1.88815 | 40.76 |
| 2 | 1.2815 | 1.335 | | |
| 3 | −2.7347 | 0.797 | 1.51825 | 64.14 |
| 4 | −1.6935 | 0.231 | | |
| 5 | −2.1424 | 0.542 | 1.72733 | 29.23 |
| 6 | 15.3785 | 0.695 | 1.77621 | 49.60 |
| 7 | −2.5873 | 0.020 | | |
| 8 | 2.9604 | 0.718 | 1.59667 | 35.31 |
| 9 | −14.2460 | Variable | | |
| 10 | −4.4554 | 0.286 | 1.75453 | 35.33 |
| 11 | −13.9667 | Variable | | |
| 12(Stop) | ∞ | 0.020 | | |
| 13 | 2.2922 | 0.285 | 1.73429 | 28.46 |
| 14 | 1.5748 | Variable | | |
| 15 | 8.8855 | 0.760 | 1.77621 | 49.60 |
| 16 | −2.8180 | 0.032 | | |
| 17 | 5.0609 | 1.054 | 1.69979 | 55.53 |
| 18 | −1.8002 | 0.478 | 1.97189 | 17.47 |
| 19 | −26.0438 | 0.152 | | |
| 20 | ∞ | 0.320 | 1.51825 | 64.14 |
| 21 | ∞ | 0.500 | | |
| 22 | ∞ | 0.880 | 1.51825 | 64.14 |
| 23 | Imaging pickup surface ∞ | | | |

| Various data | | |
|---|---|---|
| | Normal observation state | Close observation state |
| Focal distance | 0.907 | 1.020 |
| Fno | 2.95 | 3.0 |
| Object distance | 15.0 | 2.66 |
| IH | 1.0 mm | |
| 2ω | 158° | |

-continued

| Unit mm | | |
|---|---|---|
| d9 | 0.2504 | 0.7110 |
| d11 | 0.0265 | 0.2767 |
| d14 | 1.8762 | 1.1654 |

Example 2

| Unit mm | | | | |
|---|---|---|---|---|
| Surface data | | | | |
| Surface no. | r | d | ne | vd |
| 1 | ∞ | 0.385 | 1.88815 | 40.76 |
| 2 | 1.4871 | 2.377 | | |
| 3 | ∞ | 0.500 | 1.49557 | 75.00 |
| 4 | ∞ | 0.606 | | |
| 5 | −43.4711 | 2.000 | 1.77621 | 49.60 |
| 6 | −1.9369 | 0.447 | 1.59911 | 39.24 |
| 7 | −10.2589 | 0.020 | | |
| 8 | 2.7843 | 0.717 | 1.59667 | 35.31 |
| 9 | −27.1989 | 0.406 | | |
| 10(Stop) | ∞ | Variable | | |
| 11 | −4.6572 | 0.240 | 1.51977 | 52.43 |
| 12 | −34.2554 | Variable | | |
| 13 | 4.3339 | 0.180 | 1.70442 | 30.13 |
| 14 | 1.4414 | 0.478 | 1.48915 | 70.23 |
| 15 | 2.1269 | Variable | | |
| 16 | 2.6219 | 0.638 | 1.77621 | 49.60 |
| 17 | −6.8528 | 0.606 | | |
| 18 | −3.6963 | 0.874 | 1.69979 | 55.53 |
| 19 | −1.7059 | 0.478 | 1.93429 | 18.90 |
| 20 | −3.3679 | 0.200 | | |
| 21 | ∞ | 0.450 | 1.51825 | 64.14 |
| 22 | ∞ | 0.821 | | |
| 23 | ∞ | 0.550 | 1.88815 | 40.76 |
| 24 | Imaging pickup surface ∞ | | | |

| Various data | | |
|---|---|---|
| | Normal observation state | Close observation state |
| Focal distance | 1.174 | 1.242 |
| Fno | 4.92 | 5.42 |
| Object distance | 26.3 | 3.35 |
| IH | 1.0 mm | |
| 2ω | 120.8° | |
| d10 | 0.16 | 0.3448 |
| d12 | 0.02 | 0.2955 |
| d15 | 0.6962 | 0.2359 |

Example 3

| Unit mm | | | | |
|---|---|---|---|---|
| Surface data | | | | |
| Surface no. | r | d | ne | vd |
| 1 | ∞ | 0.380 | 1.88815 | 40.76 |
| 2 | 1.1477 | 1.498 | | |
| 3 | ∞ | 0.500 | 1.51825 | 64.14 |
| 4 | ∞ | 0.606 | | |
| 5 | −6.4863 | 2.000 | 1.77621 | 49.60 |
| 6 | −1.5836 | 0.450 | 1.59911 | 39.24 |
| 7 | −4.0682 | 0.020 | | |
| 8 | 5.5995 | 0.717 | 1.59667 | 35.31 |
| 9 | −7.9918 | Variable | | |
| 10 | −6.4172 | 0.240 | 1.51977 | 52.43 |
| 11 | −34.2554 | 0.020 | | |
| 12(Stop) | ∞ | Variable | | |
| 13 | 11.9362 | 0.300 | 1.59667 | 35.31 |
| 14 | 2.3063 | Variable | | |
| 15 | 4.2276 | 0.638 | 1.77621 | 49.60 |
| 16 | 11.0452 | 0.215 | | |
| 17 | 3.4879 | 1.850 | 1.48915 | 70.23 |
| 18 | −1.7623 | 0.478 | 1.93429 | 18.90 |
| 19 | −3.0209 | 0.391 | | |
| 20 | ∞ | 0.500 | 1.51825 | 64.14 |
| 21 | ∞ | 2.229 | | |
| 22 | ∞ | 0.800 | 1.88815 | 40.76 |
| 23 | Imaging pickup surface ∞ | | | |

| Various data | | |
|---|---|---|
| | Normal observation state | Close observation state |
| Focal distance | 1.064 | 1.309 |
| Fno | 3.92 | 4.69 |
| Object distance | 26.3 | 2.22 |
| IH | 1.0 mm | |
| 2ω | 153.4° | |
| d9 | 0.115 | 0.502 |
| d12 | 0.0333 | 0.7842 |
| d14 | 1.5 | 0.3621 |

Example 4

| Unit mm | | | | |
|---|---|---|---|---|
| Surface data | | | | |
| Surface no. | r | d | ne | vd |
| 1 | ∞ | 0.380 | 1.88815 | 40.76 |
| 2 | 1.2649 | 1.323 | | |
| 3 | −3.4997 | 0.797 | 1.51825 | 64.14 |
| 4 | −1.6811 | 0.126 | | |
| 5 | −1.9395 | 0.542 | 1.72733 | 29.23 |
| 6 | 19.3591 | 1.036 | 1.77621 | 49.60 |
| 7 | −2.5749 | 0.020 | | |
| 8 | 2.6839 | 0.718 | 1.59667 | 35.31 |
| 9 | −10.7355 | Variable | | |
| 10 | −3.7069 | 0.286 | 1.75453 | 35.33 |
| 11 | −9.7789 | Variable | | |
| 12(Stop) | ∞ | 0.020 | | |
| 13 | 2.9773 | 0.285 | 1.73429 | 28.46 |
| 14 | 1.7166 | Variable | | |
| 15 | 5.7655 | 0.760 | 1.77621 | 49.60 |
| 16 | −3.1662 | 0.032 | | |
| 17 | 6.5961 | 1.054 | 1.69979 | 55.53 |
| 18 | −1.7956 | 0.478 | 1.97189 | 17.47 |
| 19 | −35.2137 | 0.157 | | |
| 20 | ∞ | 0.320 | 1.51825 | 64.14 |
| 21 | ∞ | 0.500 | | |
| 22 | ∞ | 0.880 | 1.51825 | 64.14 |
| 23 | Imaging pickup surface ∞ | | | |

-continued

Unit mm

Various data

|  | Normal observation state | Close observation state |
|---|---|---|
| Focal distance | 0.937 | 1.024 |
| Fno | 3.15 | 3.16 |
| Object distance | 15 | 3.66 |
| IH | 1.0 mm | |
| 2ω | 155.3° | |
| d9 | 0.2036 | 0.3402 |
| d11 | 0.02 | 0.526 |
| d14 | 1.7759 | 1.1333 |

Example 5

Unit mm

Surface data

| Surface no. | r | d | ne | vd |
|---|---|---|---|---|
| 1 | ∞ | 0.383 | 1.88815 | 40.76 |
| 2 | 1.2260 | 1.379 | | |
| 3 | ∞ | 0.350 | 1.88815 | 40.76 |
| 4 | ∞ | 0.480 | | |
| 5 | −8.7232 | 1.600 | 1.77621 | 49.60 |
| 6 | −2.5072 | 0.320 | 1.58482 | 40.75 |
| 7 | −3.5270 | 0.020 | | |
| 8 | 5.4575 | 0.717 | 1.59667 | 35.31 |
| 9 | −4.8801 | Variable | | |
| 10 | −5.2079 | 0.300 | 1.51825 | 64.14 |
| 11 | −4.7433 | 0.240 | 1.51977 | 52.43 |
| 12 | −34.2554 | 0.100 | | |
| 13(Stop) | ∞ | Variable | | |
| 14 | 8.7235 | 0.300 | 1.59667 | 35.31 |
| 15 | 1.1844 | 0.650 | 1.49846 | 81.54 |
| 16 | 4.1376 | Variable | | |
| 17 | 2.9597 | 0.638 | 1.77621 | 49.60 |
| 18 | −7.5247 | 0.239 | | |
| 19 | 10.4640 | 1.000 | 1.48915 | 70.23 |
| 20 | −2.5938 | 0.350 | 1.93429 | 18.90 |
| 21 | −21.5658 | 0.150 | | |
| 22 | ∞ | 0.550 | 1.51825 | 64.14 |
| 23 | ∞ | 0.596 | | |
| 24 | ∞ | 0.800 | 1.88815 | 40.76 |
| 25 | Imaging pickup surface ∞ | | | |

Various data

|  | Normal observation state | Close observation state |
|---|---|---|
| Focal distance | 1.089 | 1.157 |
| Fno | 3.56 | 3.81 |
| Object distance | 26.3 | 3.65 |
| IH | 1.0 mm | |
| 2ω | 135° | |
| d9 | 0.15 | 0.3633 |
| d13 | 0.0212 | 0.618 |
| d16 | 0.9745 | 0.1644 |

Example 6

Unit mm

Surface data

| Surface no. | r | d | ne | vd |
|---|---|---|---|---|
| 1 | ∞ | 0.340 | 1.88815 | 40.76 |
| 2 | 1.3383 | 1.078 | | |
| 3 | 6.0440 | 0.450 | 1.48915 | 70.23 |
| 4 | 2.0791 | 0.843 | | |
| 5 | 14.1820 | 1.600 | 1.77621 | 49.60 |
| 6 | −1.6879 | 0.320 | 1.58482 | 40.75 |
| 7 | −4.5957 | 0.020 | | |
| 8 | 4.0754 | 0.717 | 1.59667 | 35.31 |
| 9 | −8.6881 | Variable | | |
| 10 | −19.9927 | 0.400 | 1.85504 | 23.78 |
| 11 | 6.0323 | 0.200 | | |
| 12(Stop) | ∞ | Variable | | |
| 13 | 7.0194 | 0.300 | 1.64268 | 44.87 |
| 14 | 1.2018 | 0.650 | 1.49846 | 81.54 |
| 15 | 4.6383 | Variable | | |
| 16 | 3.0725 | 0.800 | 1.77621 | 49.60 |
| 17 | −6.8430 | 0.241 | | |
| 18 | 10.9631 | 1.500 | 1.53947 | 74.70 |
| 19 | −2.0587 | 0.350 | 1.97189 | 17.47 |
| 20 | −5.0060 | 0.116 | | |
| 21 | ∞ | 0.500 | 1.51825 | 64.14 |
| 22 | ∞ | 0.800 | | |
| 23 | ∞ | 0.550 | 1.88815 | 40.76 |
| 24 | Imaging pickup surface ∞ | | | |

Various data

|  | Normal observation state | Close observation state |
|---|---|---|
| Focal distance | 1.084 | 1.176 |
| Fno | 3.42 | 3.48 |
| Object distance | 26.3 | 3 |
| IH | 1.0 mm | |
| 2ω | 130° | |
| d9 | 0.15 | 0.57 |
| d12 | 0.3435 | 0.256 |
| d15 | 0.5685 | 0.236 |

Example 7

Unit mm

Surface data

| Surface no. | r | d | ne | vd |
|---|---|---|---|---|
| 1 | ∞ | 0.340 | 1.88815 | 40.76 |
| 2 | 1.3136 | 1.173 | | |
| 3 | ∞ | 0.450 | 1.51825 | 64.14 |
| 4 | ∞ | 1.040 | | |
| 5 | −22.0438 | 1.600 | 1.77621 | 49.60 |
| 6 | −1.9707 | 0.320 | 1.58482 | 40.75 |
| 7 | −5.4934 | 0.020 | | |
| 8 | 3.1357 | 0.717 | 1.59667 | 35.31 |
| 9 | −11.8675 | Variable | | |
| 10 | −29.3373 | 0.400 | 1.85504 | 23.78 |
| 11 | 5.4879 | 0.100 | | |
| 12(Stop) | ∞ | Variable | | |
| 13 | 146.8933 | 0.300 | 1.67340 | 47.23 |
| 14 | 1.2019 | 0.650 | 1.53947 | 74.70 |
| 15 | 27.7287 | Variable | | |
| 16 | 3.1252 | 1.200 | 1.77621 | 49.60 |

-continued

Unit mm

| | | | | |
|---|---|---|---|---|
| 17 | −11.8652 | 0.241 | | |
| 18 | 11.7363 | 1.500 | 1.53947 | 74.70 |
| 19 | −2.0431 | 0.350 | 1.97189 | 17.47 |
| 20 | −4.0454 | 0.124 | | |
| 21 | ∞ | 0.350 | 1.51825 | 64.14 |
| 22 | ∞ | 0.934 | | |
| 23 | ∞ | 0.800 | 1.88815 | 40.76 |
| 24 | Imaging pickup surface ∞ | | | |

Various data

| | Normal observation state | Close observation state |
|---|---|---|
| Focal distance | 1.124 | 1.248 |
| Fno | 3.48 | 3.56 |
| Object distance | 26.3 | 2.48 |
| IH | 1.0 mm | |
| 2ω | 130.8° | |
| d9 | 0.15 | 0.6298 |
| d12 | 0.3002 | 0.2621 |
| d15 | 0.7108 | 0.2691 |

Example 8

Unit mm

Surface data

| Surface no. | r | d | ne | vd |
|---|---|---|---|---|
| 1 | ∞ | 0.340 | 1.88815 | 40.76 |
| 2 | 1.2866 | 1.200 | | |
| 3 | ∞ | 0.450 | 1.51825 | 64.14 |
| 4 | ∞ | 0.930 | | |
| 5 | −9.2138 | 1.600 | 1.77621 | 49.60 |
| 6 | −2.1791 | 0.320 | 1.79192 | 25.68 |
| 7 | −3.2640 | 0.020 | | |
| 8 | 3.0261 | 0.717 | 1.65222 | 33.79 |
| 9 | 201.4069 | Variable | | |
| 10 | 2.9154 | 0.400 | 1.93429 | 18.90 |
| 11 | 1.7853 | 0.200 | | |
| 12(Stop) | ∞ | Variable | | |
| 13 | −8.4150 | 0.300 | 1.67340 | 47.23 |
| 14 | 1.4007 | 0.650 | 1.53947 | 74.70 |
| 15 | −12.4275 | Variable | | |
| 16 | 2.9859 | 1.200 | 1.77621 | 49.60 |
| 17 | −14.1885 | 0.240 | | |
| 18 | 12.7780 | 1.500 | 1.53947 | 74.70 |
| 19 | −1.9349 | 0.350 | 1.97189 | 17.47 |
| 20 | −3.8880 | 1.120 | | |
| 21 | ∞ | 0.700 | 1.88815 | 40.76 |
| 22 | Imaging pickup surface ∞ | | | |

Various data

| | Normal observation state | Close observation state |
|---|---|---|
| Focal distance | 1.109 | 1.219 |
| Fno | 3.02 | 3.03 |
| Object distance | 26.3 | 2.18 |
| IH | 1.0 mm | |
| 2ω | 133.9° | |

-continued

Unit mm

| | | |
|---|---|---|
| d9 | 0.15 | 0.7358 |
| d12 | 0.2444 | 0.1052 |
| d15 | 0.6918 | 0.2452 |

Table 1 below shows the values corresponding to the conditional expressions (1) to (16) in the configuration of each embodiment.

TABLE 1

Conditional expression

| | Example1 | Example2 | Example3 | Example4 |
|---|---|---|---|---|
| (1) | 0.508 | 0.157 | 0.364 | 0.146 |
| (2) | 0.783 | 0.392 | 1.07 | 0.686 |
| (3) | 0.648 | 0.401 | 0.34 | 0.213 |
| (4) | −1.59 | −1.426 | −1.215 | −1.52 |
| (5) | 2.498 | 2.328 | 2.549 | 2.138 |
| (6) | 1.657 | 1.062 | 1.252 | 1.234 |
| (7) | −9.681 | −8.855 | −14.326 | −8.62 |
| (8) | −9.079 | −4.072 | −4.557 | −6.517 |
| (9) | 2.712 | 2.569 | 3.45 | 2.792 |
| (10) | 3.422 | 1.062 | 1.942 | 2.231 |
| (11) | 3.012 | 5.617 | 4.656 | 3.331 |
| (12) | 1.066 | 2.175 | 3.143 | 1.323 |
| (13) | 1.637 | 2.42 | 2.756 | 2.262 |
| (14) | −3.348 | −1.585 | −1.321 | −2.334 |
| (15) | 2.981 | 4.92 | 3.921 | 3.15 |
| (16) | 0.993 | 0.907 | 0.836 | 0.997 |

Conditional expression

| | Example5 | Example6 | Example7 | Example8 |
|---|---|---|---|---|
| (1) | 0.196 | 0.387 | 0.427 | 0.528 |
| (2) | 0.744 | 0.307 | 0.393 | 0.403 |
| (3) | 0.263 | 1.263 | 1.086 | 1.312 |
| (4) | −1.268 | −1.39 | −1.316 | −1.306 |
| (5) | 2.26 | 2.124 | 2.173 | 2.228 |
| (6) | 1.361 | 1.221 | 1.181 | 1.237 |
| (7) | −10.918 | −4.964 | −4.785 | −5.361 |
| (8) | −6.902 | −6.918 | −7.001 | −6.949 |
| (9) | 2.867 | 2.457 | 2.621 | 2.674 |
| (10) | 2.31 | 4.813 | 4.419 | 3.426 |
| (11) | 4.26 | 3.269 | 3.149 | 3.094 |
| (12) | 1.582 | 0.718 | 0.683 | 0.771 |
| (13) | 2.107 | 2.013 | 2.218 | 2.161 |
| (14) | −2.407 | −2.815 | −2.672 | −2.599 |
| (15) | 3.557 | 3.42 | 3.483 | 3.019 |
| (16) | 0.934 | 0.982 | 0.978 | 0.997 |

Although a variety of embodiments of the present disclosure have been explained above, the present disclosure is not limited to these embodiments, and an embodiment configured by combining the configurations of these embodiments as appropriate without departing from the spirit thereof falls within the range of the present disclosure.

APPENDIX

A disclosure having the following configuration is derived from these examples.

[Appended Mode 1]

An objective optical system using, in order from an object side: a positive first group; a negative second group; a negative third group; and a positive fourth group, wherein the second group and the third group move together toward an image side to perform focusing from an object point at a long distance to an object point at a close distance, and the following conditional expression (1) is satisfied:

$$0.1<(t12n-t12f)/F<1.2 \quad (1)$$

where t12n is a distance between the first group and the second group at a time of focusing to the object point at the close distance, t12f is a distance between the first group and the second group at a time of focusing to the object point at the long distance, and F is a focal length of the overall objective optical system at a time of focusing to the object point at the long distance.

[Appended Mode 2]

The objective optical system according to appended mode 2, wherein the following conditional expression (2) is satisfied:

$$0.2<(t34f-t34n)/F<2 \quad (2)$$

where t34f is a distance between the third group and the fourth group at a time of focusing to the object point at the long distance, t34n is a distance between the third group and the fourth group at a time of focusing to the object point at the close distance, and F is a focal length of the overall objective optical system at a time of focusing to the object point at the long distance.

[Appended Mode 3]

The objective optical system according to appended mode 1, wherein at least one conditional expression of the following conditional expressions (3), (4), and (5) is satisfied:

$$0.1<(t12n-t12f)/(t34f-t34n)<2.2 \quad (3)$$

$$-1<fG1-1/F<-2 \quad (4)$$

$$1.8<fG1-2/F<3.5 \quad (5)$$

where t12n is a distance between the first group and the second group at a time of focusing to the object point at the close distance, t12f is a distance between the first group and the second group at a time of focusing to the object point at the long distance, t34f is a distance between the third group and the fourth group at a time of focusing to the object point at the long distance, t34n is a distance between the third group and the fourth group at a time of focusing to the object point at the close distance, fG1-1 is a focal length of a lens nearest to the object in the first group, fG1-2 is a focal length of a positive sub-lens group subsequent to the lens nearest to the object in the first group, and F is a focal length of the overall objective optical system at a time of focusing to the object point at the long distance.

[Appended Mode 4]

The objective optical system according to any one of appended modes 1 to 3, wherein at least one conditional expression of the following conditional expressions (6), (7), (8), (9), (10), (11), (12), (13), (14), (15), and (16) is satisfied:

$$0.6<fG1/F<2.2 \quad (6)$$

$$-18<fG2/F<-4.5 \quad (7)$$

$$-10<fG3/F<-3 \quad (8)$$

$$1<fG4/F<5 \quad (9)$$

$$1<fG1S/F<8 \quad (10)$$

$$2<fGS4/F<7 \quad (11)$$

$$0.5<fG2/fG3<3.5 \quad (12)$$

$$1.5<fG4/fG1<3.5 \quad (13)$$

$$-4<fG3/fG4<-1 \quad (14)$$

$$2.5<Fno<5.2 \quad (15)$$

$$0.8<Fno/Fno\_N<1.2 \quad (16)$$

where

F is a focal length of the overall objective optical system at a time of focusing to the object point at the long distance, fG1 is a focal length of the first group, fG2 is a focal length of the second group, fG3 is a focal length of the third group, fG4 is a focal length of the fourth group, fG1S is a combined focal length from the first group to an aperture stop at a time of focusing to the object point at the long distance, fGS4 is a combined focal length from the aperture stop to the fourth group at a time of focusing to the object point at the long distance, Fno is an F value of the objective optical system at a time of focusing to the object point at the long distance, and Fno_N is an F value of the objective optical system at a time of focusing to the object point at the close distance.

[Appended Mode 5].

The objective optical system according to any one of appended modes 1 to 4, wherein at least one conditional expression of the following conditional expressions (1'), (2'), (2"), (3'), (5'), (6'), (9'), (10'), (11'), and (13') is satisfied:

$$0.1<(t12n-t12f)/F<0.7 \quad (1')$$

$$0.2<(t34f-t34n)/F<1.6 \quad (2')$$

$$0.2<(t34f-t34n)/F<1.2 \quad (2'')$$

$$0.1<(t12n-t12f)/(t34f-t34n)<1.6 \quad (3')$$

$$2<fG1-2/F<3 \quad (5')$$

$$1<fG1/F<1.8 \quad (6')$$

$$2<fG4/F<4 \quad (9')$$

$$1<fG1S/F<5.5 \quad (10')$$

$$2.4<fGS4/F<6.2 \quad (11')$$

$$1.5<fG4/fG1<3 \quad (13')$$

where
t12n is a distance between the first group and the second group at a time of focusing to the object point at the close distance,
t12f is a distance between the first group and the second group at a time of focusing to the object point at the long distance,
t34f is a distance between the third group and the fourth group at a time of focusing to the object point at the long distance,
t34n is a distance between the third group and the fourth group at a time of focusing to the object point at the close distance,
F is a focal length of the overall objective optical system at a time of focusing to the object point at the long distance,
fG1 is a focal length of the first group,
fG4 is a focal length of the fourth group,
fG1-2 is a focal length of a positive sub-lens group subsequent to a lens nearest to the object in the first group,
fG1S is a combined focal length from the first group to an aperture stop at a time of focusing to the object point at the long distance, and
fGS4 is a combined focal length from the aperture stop to the fourth group at a time of focusing to the object point at the long distance.

Any one conditional expression among the conditional expressions may be used singly or the conditional expressions may be combined freely to achieve the advantageous effects of the present disclosure. Furthermore, a conditional expression in which an upper limit value and a lower limit value of the conditional expressions are individually changed may achieve the advantageous effects of the present disclosure, similarly.

As described above, in an objective optical system capable of focusing for magnified observation according to change in object point distance, the present disclosure is useful for an objective optical system with reduced manufacturing error sensitivity, support a high-resolution and compact image sensor, and with high performance and with a bright Fno, and an endoscope using the same.

In an objective optical system capable of focusing for magnified observation (close observation) according to change in object point distance, the present disclosure achieves the advantageous effect of providing an objective optical system with reduced manufacturing error sensitivity, support a high-resolution and compact image sensor, and with high performance and with a bright Fno.

What is claimed is:

1. An objective optical system comprising, in order from an object side:
a positive first group;
a negative second group;
a negative third group; and
a positive fourth group,
wherein:
the second group and the third group move together toward an image side to perform focusing from an object point at a long distance to an object point at a close distance,
the lens furthest to the object side, from among lenses of the positive first group, is a flat concave lens having a concave surface directed toward the image side, and
the following conditional expressions (1) and (2) are satisfied:

$$0.1 < (t12n - t12f)/F < 1.2 \quad (1),$$

$$0.2 < (t34f - t34n)/F < 2 \quad (2)$$

where:
t12n is a distance between the first group and the second group at a time of focusing to the object point at the close distance,
t12f is a distance between the first group and the second group at a time of focusing to the object point at the long distance,
t34f is a distance between the third group and the fourth group at the time of focusing to the object point at the long distance,
t34n is a distance between the third group and the fourth group at the time of focusing to the object point at the close distance, and
F is a focal length of the overall objective optical system at the time of focusing to the object point at the long distance.

2. An objective optical system comprising, in order from an object side:
a positive first group;
a negative second group;
a negative third group; and
a positive fourth group,
wherein:
the second group and the third group move together toward an image side to perform focusing from an object point at a long distance to an object point at a close distance,
the lens furthest to the object side, from among lenses of the positive first group, is a flat concave lens having a concave surface directed toward the image side, and
the following conditional expression (2) is satisfied, and at least one conditional expression of the following conditional expressions (3), (4), and (5) is satisfied:

$$0.2 < (t34f - t34n)/F < 2 \quad (2),$$

$$0.1 < (t12n - t12f)/(t34f - t34n) < 2.2 \quad (3),$$

$$-1 < fG1 - 1/F < -2 \quad (4),$$

$$1.8 < fG1 - 2/F < 3.5 \quad (5),$$

where:
t34f is a distance between the third group and the fourth group at a time of focusing to the object point at the long distance,
t34n is a distance between the third group and the fourth group at a time of focusing to the object point at the close distance,
F is a focal length of the overall objective optical system at the time of focusing to the object point at the long distance,
t12n is a distance between the first group and the second group at the time of focusing to the object point at the close distance,
t12f is a distance between the first group and the second group at the time of focusing to the object point at the long distance,
fG1-1 is a focal length of a lens nearest to the object in the first group, and
fG1-2 is a focal length of a positive sub-lens group subsequent to the lens nearest to the object in the first group.

3. An endoscope comprising the objective optical system according to claim 1.

4. An endoscope comprising the objective optical system according to claim 3.

* * * * *